(12) United States Patent
Schütze et al.

(10) Patent No.: US 10,551,321 B2
(45) Date of Patent: Feb. 4, 2020

(54) DEVICE AND METHOD FOR DETECTING AND/OR EVALUATING PATHOLOGICAL STATES

(71) Applicant: CellTool GmbH, Bernried (DE)

(72) Inventors: Karin Schütze, Tutzing (DE); Raimund Schütze, Tutzing (DE); Waldemar Lernhardt, Oberslum-Sülzbach (DE)

(73) Assignee: CellTool GmbH, Bernried (DE)

( * ) Notice: Subject to any disclaimer, the term of this patent is extended or adjusted under 35 U.S.C. 154(b) by 0 days.

(21) Appl. No.: 15/766,516

(22) PCT Filed: Oct. 7, 2016

(86) PCT No.: PCT/EP2016/073998
§ 371 (c)(1),
(2) Date: Apr. 6, 2018

(87) PCT Pub. No.: WO2017/060425
PCT Pub. Date: Apr. 13, 2017

(65) Prior Publication Data
US 2018/0292323 A1      Oct. 11, 2018

(30) Foreign Application Priority Data
Oct. 7, 2015   (DE) ........................ 10 2015 219 349

(51) Int. Cl.
*G01J 3/44*      (2006.01)
*G01N 21/65*    (2006.01)
*G06N 20/00*    (2019.01)

(52) U.S. Cl.
CPC ................ *G01N 21/65* (2013.01); *G01J 3/44* (2013.01); *G01N 2021/656* (2013.01); *G06N 20/00* (2019.01)

(58) Field of Classification Search
CPC ........ G01N 21/65; G01N 21/62; G01N 21/55; G01N 21/47; G01N 21/59; G01N 21/84;
(Continued)

(56) References Cited

U.S. PATENT DOCUMENTS

2008/0231834 A1* 9/2008 Gryczynski ............ B82Y 20/00
                                                                              356/36
2008/0319324 A1* 12/2008 Maier .................. A61B 5/0059
                                                                              600/477
(Continued)

FOREIGN PATENT DOCUMENTS

WO         2013103475          7/2013

OTHER PUBLICATIONS

Imran I. Patel et al: "High contrast images of uterine tissue derived using Raman microspectroscopy with the empty modelling approach of multivariate curve resolution-alternating least squares", The Analyst, vol. 136, No. 23, 2011, p. 4950, XP055333721, GB ISSN: 0003-2654, DOI: 10.1039/clan15717e abstract figures 1,2.
(Continued)

*Primary Examiner* — Abdullahi Nur
(74) *Attorney, Agent, or Firm* — Sand, Sebolt & Wernow Co., LPA

(57) ABSTRACT

The invention relates to a device (1) for detecting and/or evaluating a pathological condition comprising a Raman spectroscopy system (10) and an electronic evaluation device (20), which is configured to perform a detection and/or evaluation of the pathological condition in accordance with an evaluation of at least one Raman spectrum detected in stroma.

22 Claims, 13 Drawing Sheets

(58) Field of Classification Search
CPC ..... G01N 1/00; G01N 1/40; G01J 3/44; G01J 1/42; A61B 6/00
See application file for complete search history.

(56) References Cited

U.S. PATENT DOCUMENTS

2009/0002702 A1  1/2009  Maier et al.
2012/0078524 A1  3/2012  Stewart et al.

OTHER PUBLICATIONS

S. Koch et al: "Novel cell identification: markerfree and suitable for living cells", Proceedings of SPIE, vol. 8798, Jun. 18, 2013 (Jun. 18, 2013), p. 87980J, XP055191973, ISSN: 0277-786X, DOI: 10.1117/12.2033542 pp. 87980J-3, line 1-line 15.

Pu Chen et al: "Bio-Raman spectroscopy: a potential clinical analytical method assisting in disease diagnosis", Analytical Methods, vol. 3, No. 6, 2011, p. 1257, XP055333291, GBR ISSN: 1759-9660, DOI: 10.1039/clay05039g the whole document.

Beljebbar A El Al: "Identification of Raman spectroscopic markers for the characterization of normal and adenocarcinomatous colonic tissues", Critical Reviews in Oncology/Hematology, Elsevier, Amsterdam, NL, vol. 72, No. 3, 2009, pp. 255-264, XP026751387, ISSN: 1040-8428, DOI: 10.1016/J.CRITREVONC.2009.09.004 [retrieved on Oct. 9, 2009] the whole document.

Matthew Tollefson et al: "Raman spectral imaging of prostate cancer: Can Raman molecular imaging be used to augment standard histopathology?", BJU International, vol. 106, No. 4, 2010, pp. 484-488, xp055197347, ISSN: 1464-4096, DOI:10.1111/j.1464-140X.2010.09185.x Title Abstract p. 484 R-hand col ln 12-17, p. 485 L-hand col ln 39-M-col ln 9, p. 485 R-hand col ln 1-7, p. 485 R-hand col ln 21-50, p. 486 L-hand col ln 15-17, p. 486 R-hand col ln18, p. 487 M-col ln 29-40, Figure 2.

\* cited by examiner

DEVICE AND METHOD FOR DETECTING AND/OR EVALUATING PATHOLOGICAL STATES

AREA OF INVENTION

The invention relates to devices and methods for the detection and/or machine-based assessment of pathological conditions. The invention relates in particular to devices and methods for the detection and/or assessment of tumors based on an evaluation of at least one Raman spectrum. In particular, the invention relates to devices and methods by which a sample, for example a biopsy, a tissue section, blood, urine, lymphatic fluid, interstitial fluid or ejaculate is quantitatively evaluated to detect whether an aggressive or a non-aggressive tumor is present.

BACKGROUND

The timely detection of tumors with a determination of whether it is a malignant or benign tumor is of considerable importance. Various techniques are known. A digital rectal examination may result in a suspicion for the presence of prostate cancer. For a quantitative examination ultrasound examination, magnetic resonance tomography or positron emission tomography (PET) can be used. In addition, biomarkers, such as protein biomarkers, can aid in the detection and differentiation of malignant tumors and benign tumors. For example, some of these biomarkers can be detected in the blood, urine or ejaculate. Through the examination of a biopsied tissue sample it is determined, on the basis of said tissue sample, whether an aggressive tumor is present. The detection of tumors, and the determination of whether an aggressive tumor or non-aggressive tumor is present is of particular importance for the decision whether further observation (so-called "active surveillance") is indicated, or whether therapies such as a prostatectomy, radiation therapy, hormone therapy or chemotherapy must be performed.

Efficient and objective examination of samples, such as blood, urine, ejaculate, lymphatic fluid, interstitial fluid, biopsies or tissue sections, remains a challenge, however. Many of the traditional approaches to assaying the samples are cumbersome, costly, and often not sufficiently objective.

In particular, the study of biopsies often has the problem that biopsy tissue, especially for small tumors may only contain tissue that contains no tumor cells or that it is far away from the tumor. In these cases, conventional examination methods often do not allow sufficiently reliable knowledge as to whether an aggressive or non-aggressive tumor is present.

SUMMARY OF THE INVENTION

There is a need for devices and methods for assaying a sample that allow the detection of pathological conditions. In particular, there is a need for such devices and methods, which enable quantitative measurements in an objective way and allow statements about a tumor, for example, by determining whether an aggressive or a non-aggressive tumor is present. More specifically, there is a need for such devices and methods that are applicable even when taking measurements outside the tumor.

According to embodiments of the invention, a Raman spectroscopy is performed to examine a sample. One or more Raman spectra detected in tumor stroma can be analyzed and said spectra are used to determine from Raman spectra or a location-dependent change in Raman spectra a spectral fingerprint indicating whether an aggressive or non-aggressive tumor is present. For example, one or more Raman spectra can be analyzed, in order to detect, on the basis of the pattern of Raman peaks, tumors and optionally their aggressiveness, and/or to determine their spatial distribution. The sample can be a tissue sample, for example from a biopsy or a tissue section.

By evaluating one or more Raman spectrum/a the sample may be objectively and quantitatively examined. A comparison with reference data retrieved from a databank may be carried out in order to determine whether a malignant or benign tumor is present. Additional information may be obtained from the Raman spectra, for example about the aggressiveness or the stage of the tumor (so-called "grading", "staging" or "scoring").

The reference data can be obtained from the Raman spectra of tissue samples of organs taken by tonsillectomy, biopsies, cancer cells from cell cultures or by measuring the Raman spectra of biomarkers. The reference data can be determined from Raman spectra of the stroma inside or outside the tumor. The reference data may include or be derived from reference spectra that depend on both Raman spectra of normal tissue and Raman spectra of cancer-containing tissue. Corresponding reference spectra can be created for stroma and/or for tissues that are not stroma of the tumor.

According to one embodiment, a device is provided for the detection and/or assessment of a pathological condition. The device comprises a Raman spectroscopy system and an electronic evaluation device, which is configured, in order to detect and/or assess the pathological condition, depending on the evaluation of at least one Raman spectrum detected in stroma.

The electronic evaluation device may be configured to perform the detection and/or assessment of the tumor, depending on the evaluation of a Raman spectrum detected in the stroma outside a tumor.

The electronic evaluation device may be configured to perform a grading, staging or scoring of a tumor depending on the at least one Raman spectrum.

The electronic evaluation device may be configured to determine, depending on the at least one Raman spectrum, whether a tumor is aggressive or not aggressive.

The electronic evaluation device can be configured to retrieve the reference data for detecting and/or evaluating the tumor depending on the tumor type of the tumor. For different tissues, such as breast, pancreas, intestine, lung, thyroid, stomach and/or ovary, associated reference data can be stored respectively, with which, for the determination of the aggressiveness of a tumor, at least one Raman spectrum detected in a stroma outside the respective tumor can be compared.

The device may be configured to detect and/or automatically assess a breast tumor, a pancreatic tumor, a colon tumor, a lung tumor, a thyroid tumor, a stomach tumor and/or an ovarian tumor.

The electronic evaluation device can be configured to detect endometriosis via evaluation of the at least one Raman spectrum detected in the stroma tissue of an endometrium sample.

The electronic evaluation device can be configured to apply a support vector machine to data obtained from the at least one Raman spectrum.

The electronic evaluation device can be configured to subject the at least one Raman spectrum to a principal component analysis and to apply the support vector machine to identified major components.

The support vector machine can have a linear kernel.

The device may include a sample holder for holding a sample for Raman spectroscopy, wherein the device is configured to apply an excitation beam of the Raman spectroscopy system from a lower side of the sample holder to the sample.

The device can comprise a camera for capturing an image of the sample from above said sample.

A method for detecting and/or evaluating a pathological condition according to an embodiment comprises the detection of at least one Raman spectrum. The method involves the evaluation of at least one Raman spectrum by an electronic computing device, wherein at least one Raman spectrum detected in stroma is evaluated by the electronic computing device for the detection and/or assessment of the pathological condition.

In the method, the detection and/or assessment of the tumor can take place, based on the evaluation of a Raman spectrum detected in the stroma outside a tumor.

In the method, the electronic computing device can perform a grading, staging or scoring of a tumor depending on the at least one Raman spectrum.

In the method, the electronic evaluation device determines, depending on the at least one Raman spectrum, whether a tumor is aggressive or non-aggressive.

In the method, the electronic evaluation device can retrieve reference data used for the detection and/or assessment of the tumor, depending on a tumor type of the tumor.

The method can be used to automatically detect and/or assess a breast tumor using one or more Raman spectra detected in a stroma.

The method can be used to automatically detect and/or evaluate a pancreatic tumor using one or more Raman spectra detected in a stroma.

The method can be used to automatically detect and/or assess a colon tumor using one or more Raman spectra detected in a stroma.

The method can be used to automatically detect and/or assess a lung tumor using one or more Raman spectra detected in a stroma.

The method can be used to automatically detect and/or assess a thyroid tumor using one or more Raman spectra detected in a stroma.

The method can be used to automatically detect and/or assess a stomach tumor using one or more Raman spectra detected in a stroma.

The method can be used to automatically detect and/or evaluate an ovarian tumor using one or more Raman spectra detected in a stroma.

In the method, the electronic evaluation device can detect an endometriosis by the evaluation of the at least one Raman spectrum detected in the stroma of an endometrium.

In the method, the electronic evaluation device can use a support vector machine on data obtained from the at least one Raman spectrum.

In the method, the electronic evaluation device can subject the at least one Raman spectrum to a principal component analysis and apply the support vector machine to identified major components.

The support vector machine can have a linear kernel.

During the detection of the at least one Raman spectrum the excitation beam of the Raman spectroscopy system can be applied from a lower side of a sample holder to the sample.

In the method, an image of a sample at which the Raman spectra are recorded can be recorded with a camera from above.

A device for detecting a tumor according to an embodiment can be used in Raman spectroscopy system to capture at least one Raman spectrum of a sample, wherein at least one Raman spectrum can be detected in the stroma of a tumor, especially outside the tumor. The device comprises an electronic evaluation device which is configured to recognize the tumor according to an evaluation of at least one Raman spectrum.

The electronic evaluation device can be configured to detect by the evaluation of at least one Raman spectrum, whether an aggressive tumor or a non-aggressive tumor is present. The electronic evaluation device can be configured to evaluate an intensity of the Raman signal at at least one wave number, which is assigned to a biomarker for an aggressive tumor or for a non-aggressive tumor.

The electronic evaluation device can be configured to detect, by the evaluation of the at least one Raman spectrum, whether the tumor is malignant. The electronic evaluation device can be configured to detect, by the evaluation of the at least one Raman spectrum, if the tumor is malignant (aggressive), even if a Gleason score of for example 6 does not allow a clear assignment to malignant or not malignant tumor.

The electronic evaluation device can be configured to detect an aggressiveness of the tumor by evaluating the at least one Raman spectrum. The electronic evaluation device may be configured to perform an assessment of a malignant tumor (so-called "grading" of the tumor) by the evaluation of the at least one Raman spectrum.

The electronic evaluation device can be configured to determine by the evaluation of the at least one Raman spectrum which stage the tumor is assigned (so-called "staging" of the tumor).

The device can be configured to capture at least one Raman spectrum at a plurality of positions of a tissue sample. The device may comprise at least one controllable motor to induce a relative movement between the sample and optical components of the Raman spectroscopy system in order to automatically capture Raman spectra at a plurality of positions of the tissue sample. The majority of positions and the spacing can also be user-defined. The majority of positions and the distances can be determined automatically by the system, for example by means of appropriate configurations, which can be implemented in hardware, software or firmware.

The device can be configured to set the plurality of positions such that individual cells in a tissue sample can be captured each by one Raman spectrum. Alternatively, or in addition, the device may be configured to set a plurality of sample positions so that for individual subcellular areas, for example for nuclei and cytoplasm, a Raman spectrum is recorded in a tissue sample.

The device may comprise at least one controllable motor to induce a relative movement between the sample and optical components of the Raman spectroscopy system, in order to automatically capture Raman spectra at the majority of positions of the tissue sample. The majority of sampling positions can also be user-defined.

The electronic evaluation device can be configured to evaluate the Raman spectra recorded on the majority of sample positions. This allows for the automatic detection of Raman peaks that are associated with benign or malignant tumors.

The electronic evaluation device may be configured in order to provide a statistical analysis for the Raman spectra covered by the majority of positions, for example a principal component analysis (PCA) or perform a hierarchical or non-hierarchical cluster analysis.

Based on the results of the statistical analysis, the electronic evaluation device can assess whether there is an aggressive or non-aggressive tumor. The principal component analysis or cluster analysis can allow for an automatic differentiation of aggressive or non-aggressive tumors using the Raman spectra.

The electronic evaluation device may be configured to determine a location-dependent change of a Raman signal from the Raman spectra recorded on the majority of sample positions to determine whether there is an aggressive or non-aggressive tumor. The location-dependent change of the Raman signal of at least one biomarker for aggressive tumors can be detected to determine whether an aggressive tumor or a non-aggressive tumor is present. It is possible to determine the location-dependent change of the result of the statistical analysis of the Raman spectra recorded in several positions in order to determine whether an aggressive tumor or a non-aggressive tumor is present. In this way, the entirety of the Raman spectrum can determine whether an aggressive or non-aggressive tumor is present. An assignment of Raman peaks to individual biomarkers is possible, but not strictly necessary. A differentiation between aggressive and non-aggressive tumors is possible in a simple way. In particular, an analysis of a Raman spectrum or several Raman spectra, which are or will be detected in tissues, urine, blood, ejaculate or derived substances, can determine whether an aggressive or a non-aggressive tumor is present.

A distinction between aggressive or non-aggressive tumors can be made without the need to allocate individual Raman peaks to biomarkers or other substances. Rather, the pattern of Raman peaks can be evaluated which, in order to distinguish aggressive and non-aggressive tumors, allows grading, staging or scoring automatically. It can be determined from the whole of the Raman spectrum, whether an aggressive or non-aggressive tumor is present. Using a statistical analysis, such as a PCA or clustering techniques, a pattern or multiple patterns in the spectrum can be used as a differentiation criterion for distinguishing aggressive and non-aggressive tumors. Such patterns can be defined by the location of several Raman peaks, their height, and/or the steepness of the flanks.

Alternatively, or additionally, the reaction of cells of the diseased organ, stroma cells or other constituents of the sample can be detected on substances produced by a tumor.

The electronic evaluation device can be configured to determine a gradient of local change in a spatially resolved manner. The gradient can be a gradient of an intensity, i.e. the amplitude, of a Raman peak. The gradient can be a gradient of a height, flank steepness of Raman peaks and/or combination of peaks. The gradient can be a gradient of a location of the result of a principal component analysis or a hierarchical or non-hierarchical cluster analysis in a multi-dimensional data area. This may result in an assessment of the tumor carried out by the electronic evaluation device. Alternatively, or additionally, conclusions can be drawn on the position of the malignant tumor.

The electronic evaluation device can be configured to determine the gradient in a spatially resolved manner.

The electronic evaluation device may be configured to establish a position of the tumor in the tissue sample or relative to the tissue sample by evaluation of the Raman spectra covered by the majority of sample positions. The electronic evaluation device may be configured to determine the position of a malignant tumor based on the spatial change of Raman signals even if no cancer cells are included in the tissue sample. The electronic evaluation device may be configured to determine the position of an aggressive tumor based on the local change of Raman signals even if the tissue sample is a tissue sample of the stroma outside and/or inside the tumor.

The electronic evaluation device can be configured to compare the Raman spectra recorded at a majority of the sample positions with stored reference spectra. The reference spectra can contain spatially resolved Raman spectra of samples with malignant tumors, of samples with non-aggressive tumors and/or of samples without tumors.

The electronic evaluation device can be configured to subject the Raman spectra recorded on the majority of the sample positions to a statistical analysis, for example a main component analysis or a hierarchical or non-hierarchical cluster analysis and compare the results with a statistical analysis of reference spectra.

The tissue sample can be a histological cut of a biopsy specimen. The biopsy can be a biopsy obtained by punch biopsy.

The tissue sample may be a histological cut of a part or several parts of a surgically removed tissue.

The device can be configured to record Raman spectra from tissue specimens of several biopsies in a spatially resolved manner for each. The Raman spectra evaluated for the multiple biopsy specimens can be used to determine whether a benign tumor or malignant tumor is present. The Raman spectra evaluated for the multiple biopsy specimens can be used to determine whether an aggressive tumor or a non-aggressive tumor is present.

The biopsy can be a biopsy of the stroma of the tumor. The biopsy can be a biopsy of the stroma outside the tumor.

The sample can be blood, urine, lymphatic fluid, interstitial fluid or ejaculate or may be obtained from blood, urine, lymphatic fluid, interstitial fluid or ejaculate. The device can be configured to determine by Raman spectroscopy whether bio-molecules or biomarkers are present that indicate the presence of an aggressive tumor.

The bio-molecules that are identified with Raman spectroscopy can be DNA or proteins, i.e. genetic or molecular biomarkers or a mixture thereof. The biomarkers can be protein biomarkers. The characteristic Raman spectra derived from these can be used as a "photonic fingerprint", which provides a photonic biomarker for the detection of aggressive tumors. These can be used as a reference for further investigations. An assignment of such photonic fingerprints to individual biomarkers is possible, but not strictly necessary, for example, to distinguish aggressive from non-aggressive tumors. For example, a statistical analysis, such as a principal component analysis or a cluster analysis, can be applied to one or more acquired Raman spectra to detect whether the acquired Raman spectrum is from an aggressive or non-aggressive tumor.

The electronic evaluation device can be configured to determine the aggressiveness of the tumor based on the Raman spectrum in one or more wave numbers or wave number ranges. The one or more wave numbers or wave number ranges can be selected from single or multiple wave number groups. The wave number groups may depend on the tissue or tumor being examined.

A method for evaluating a sample to detect a tumor can comprise at least one Raman spectrum of the sample and a detection of the tumor by evaluating the at least one Raman spectrum.

The sample may be a tissue sample, for example a tissue cut of a biopsy obtained by punch biopsy.

The tissue sample can be a histological cut of a part or several parts of surgically removed tissue.

Raman spectra can be recorded at a plurality of tissue sample positions. The Raman spectra recorded in the majority of positions can be evaluated for the detection of the tumor.

For the Raman spectra recorded in the majority of positions, a statistical analysis can be carried out, for example a principal component analysis or a hierarchical or non-hierarchical cluster analysis.

The Raman spectra can be detected at a plurality of subcellular positions of the cells in a tissue sample. The Raman spectra recorded at the plurality of subcellular positions can be evaluated for the detection of the tumor.

Depending on the Raman spectra recorded in the majority of positions, a spatially resolved change of Raman signals associated with aggressive tumors can be determined. It is possible to determine the location-dependent change of the result of the statistical analysis of the Raman spectra recorded in several positions in order to determine whether an aggressive tumor or a non-aggressive tumor is present. In this way, the entire Raman spectrum can be used to determine whether an aggressive or non-aggressive tumor is present. The assignment of Raman peaks to individual biomarkers is possible, but not strictly necessary. A differentiation between aggressive and non-aggressive tumors is possible in a simple way.

Depending on the Raman spectra covered by the majority of positions, it can be determined how a biomarker changes location-dependent.

The method can be used to determine a position of the tumor in the tissue sample or relative to the tissue sample.

The method can be used to determine the aggressiveness of the tumor. To determine the aggressiveness, the result of a statistical analysis of the Raman spectrum can be compared and aligned with the results of a statistical analysis of reference spectra, which are associated with aggressive and non-aggressive tumors.

With this method one or several, "photonic fingerprints" of the sample can be obtained, which define the captured Raman intensity at a plurality of wave numbers, for example, n>100 wave numbers. An assignment of such photonic fingerprints to individual biomarkers is possible, but not strictly necessary, for example, to distinguish aggressive from non-aggressive tumors. For example, a statistical analysis, such as a principal component analysis or a cluster analysis, can be applied to one or more acquired Raman spectra to detect whether the acquired Raman spectrum is associated with an aggressive or non-aggressive tumor.

In the methods and devices, a support vector machine (SVM) can be used to further process the result of a principal component analysis.

The method can be executed automatically by the device according to an embodiment.

The methods according to the embodiments can be carried out far from the human or animal body. The device according to the embodiments can be used for an examination of the sample, wherein the examination is carried out far from the human or animal body.

The devices and methods according to the embodiments can be configured so that the extraction of the sample, in particular the extraction of a biopsy specimen or tissue cut, is not part of the claimed devices and methods.

Devices and methods according to the embodiments allow an objective detection of aggressive tumors and their differentiation from non-aggressive tumors by quantitative evaluation of at least one Raman spectrum of a sample.

Devices and methods according to the embodiments can be used to detect and/or assess tumors which are not prostate tumors.

BRIEF DESCRIPTION OF THE FIGURES

The invention is subsequently further explained by reference to the drawings of preferred embodiments.

DESCRIPTION OF THE EMBODIMENTS

Embodiments are described with reference to the figures, in which similar reference numbers denote similar features. The features of the various embodiments described can be combined, unless this is expressly excluded in the following description.

Devices and methods according to embodiments can be used to study a sample in order to detect and evaluate pathological conditions. Devices and methods according to embodiments can be used for the automatic assessment of a tumor to determine the aggressiveness of the tumor. The assessment can be made on the basis of at least one or more Raman spectra recorded on a stroma. The stroma can be located outside the tumor. Other pathological conditions, such as endometriosis, can be detected.

In the case of devices and methods according to embodiments, at least one Raman spectrum of a sample is detected. The sample may be, for example, a tissue cut of a biopsy specimen obtained by punch biopsy, a tissue cut from a surgically removed organ or other tissue, blood, urine, ejaculate, lymphatic fluid or interstitial fluid or obtained from it.

At least one Raman spectrum is evaluated to determine whether a malignant tumor is present. Additional provisions, such as for assessment ("grading") or cancer staging ("staging"), can be made on the basis of one or more Raman spectra.

Figure 1:
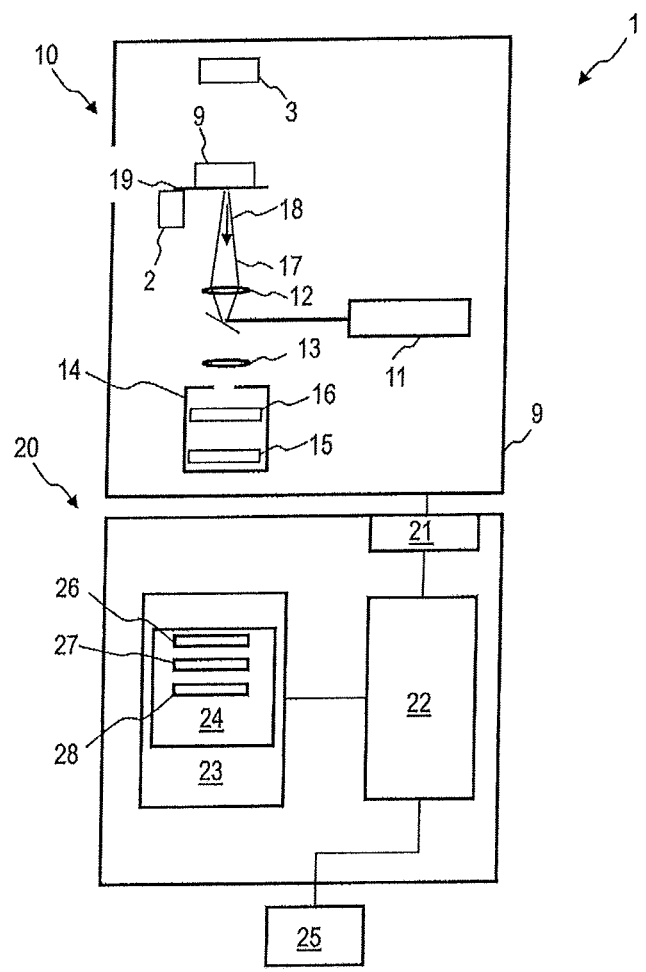
FIG. 1 shows a schematic representation of a device according to an embodiment.

FIG. 1 is a schematic representation of a device 1 according to an embodiment. The device 1 is configured to study a sample 9 with Raman spectroscopy to detect a tumor, especially a malignant tumor. The corresponding detection is carried out using at least one Raman spectrum, which the device 1 can capture and automatically evaluate.

The device 1 comprises a Raman spectroscopy system 10 and an evaluation device 20. The Raman spectroscopy system 10 is configured to capture a Raman spectrum of sample 9. For example, the sample 9 can be obtained from blood, urine, ejaculate, biopsy or a tissue section, wherein the extraction of the sample, in particular by punch biopsy or other removal of material is not the subject of the methods according to the embodiments.

The sample 9 may contain cells of the stroma of the tumor. The sample 9 can contain cells of a breast.

The Raman spectroscopy system 10 includes a light source 11, which can in particular be a laser. The light source 11 is configured to emit an excitation beam 17. A Raman spectrometer 14 receives at the sample 9 scattered light by Stokes processes and/or anti-Stokes processes 18. The Raman spectrometer 14 can comprise a diffractive element 15 and an image sensor 16 to capture the Raman spectrum of the sample 9. The Raman spectroscopy system 10 can comprise other elements per se known in the art, for example, focusing optical elements 12, 13, which can be designed as lenses and/or apertures.

The device 1 can be configured so that the excitation beam of the Raman spectroscopy systems is directed from the underside of a sample holder 19 to the sample 9.

The device 1 can comprise an actuator 2 for the readjustment of the sample holder 19.

The device 1 can comprise a camera 3 for capturing an image from above of the sample 9. Movement control of the actuator 2 and/or the light source 11 can be based on an image captured with the camera 3.

The device 1 comprises an evaluation device 20. The evaluation device 20 can be a computer or comprise a computer. The evaluation device 20 is coupled with the Raman spectroscopy system 10. The evaluation device 20 can control the detection of the Raman spectrum by the Raman spectroscopy system 10. The evaluation device 20 can control the Raman spectroscopy system 10 so that Raman spectra are detected in a spatially resolved manner at several places of sample 9.

The evaluation device 20 has an interface 21 to receive data from the image sensor 16 of the Raman spectroscopy system 10. The evaluation device has an integrated semiconductor circuit 22, which can comprise a processor or controller and which is configured to evaluate the acquired Raman spectrum in order to determine whether a malignant tumor is present using the at least one Raman spectrum.

As is described in more detail by reference to FIG. 2 to FIG. 24, the integrated semiconductor circuit 22 can be configured to be out of the pattern of Raman peaks to detect whether a tumor is aggressive or not aggressive and/or to make a stage or grading determination. The integrated semiconductor circuit 22 can be configured, for example, to determine by evaluation of the at least one Raman spectrum detected in the stroma outside of the tumor, whether the tumor is aggressive or not aggressive to enable a grading or a stage determination.

The integrated semiconductor circuit 22 may be configured to evaluate the at least one Raman spectrum to determine quantitatively whether and in what amount biomarkers for a malignant tumor are present. The integrated semiconductor circuit 22 may be configured to determine, for a tissue sample, local spatially resolved changes and, in particular, local gradients of Raman signals associated with malignant tumors. Characteristic location-dependent changes of Raman spectra associated with an aggressive tumor can be stored in a database. The location-dependent variation of the Raman signal, for which information is stored in the database, may indicate a change in the Raman signal in the stroma outside the tumor.

The Raman peaks evaluated by the integrated semiconductor circuit 22 may be associated with molecular or genetic biomarkers. The Raman peaks evaluated by the integrated semiconductor circuit 22 may be associated with protein biomarkers.

The device 1 may be configured to optionally also determine the spatial variation of Raman spectra. Some of the characteristics of a Raman spectrum may be more severe near an aggressive tumor, while others of the characteristics are more pronounced at a distance from an aggressive tumor than in the immediate vicinity of the aggressive tumor.

The integrated semiconductor circuit 22 can process detected Raman spectra in different ways. For example, statistical methods, e.g. a principal component analysis. Other statistical methods, such as a hierarchical cluster analysis, can be used to assess whether a Raman spectrum in its entirety is attributable to an aggressive or a non-aggressive tumor. Additionally, or alternatively, Raman spectra or the location-dependent variation of at least individual Raman peaks may be compared to reference data to determine if an aggressive tumor is present. The determination of the gradient is not limited to the intensity of individual Raman peaks, but may, for example, also be performed for the distance of a data point in an N-dimensional data space by a principal component analysis of the area in the N-dimensional data space associated with an aggressive tumor. The corresponding processing can be carried out automatically by the integrated semiconductor circuit 22.

The integrated semiconductor circuit 22 may be configured to perform a support vector machine (SVC) analysis. The support vector machine can be used to differentiate between aggressive and non-aggressive tumors. The support vector machine may be applied to results of a principal component analysis of the at least one Raman spectrum to determine if the tumor is aggressive or non-aggressive.

The evaluation device 20 may comprise a memory 23, in which the reference data 24 are stored, which can use the integrated semiconductor circuit 22 in the evaluation of the Raman spectrum. The reference data 24 may include reference data sets 26-28 for different types of tumors. Reference data 24 may include reference datasets 26-28 associated with at least one of the following tumors: a breast tumor, a pancreatic tumor, a colon tumor, a lung tumor, a thyroid tumor, a stomach tumor, and/or an ovarian tumor. The reference data 24 may include reference data sets 26-28 associated with two or more of the following tumors: a breast tumor, a pancreatic tumor, a colon tumor, a lung tumor, a thyroid tumor, a stomach tumor, and/or an ovarian tumor.

Depending on which tissue sample is being examined, the integrated semiconductor circuit 22 can retrieve and use the corresponding reference data set 26-28. The reference data set can in each case specify in which areas of a principal component space data points corresponding to an aggressive tumor and data points corresponding to a non-aggressive tumor are arranged. The reference data set may each comprise information about reference Raman spectra collected at the stroma outside of aggressive tumors and collected on stroma outside of non-aggressive tumors.

The evaluation device 20 may be an optical and/or acoustic output unit which outputs information dependent on the analysis of the at least one Raman spectrum indicating whether an aggressive tumor is present. An assessment of the aggressiveness of the tumor can be issued. Thus information about a stage of a carcinoma can be obtained.

Although the evaluation device 20 and the Raman spectroscopy system 10 are shown schematically as separate units in FIG. 1, the functions of the evaluation device 20 can also be integrated in a housing of the Raman spectroscopy system 10. The Raman spectroscopy system 10 and the evaluation device 20 can be configured and used as mobile, in particular as portable units.

Figure 2:
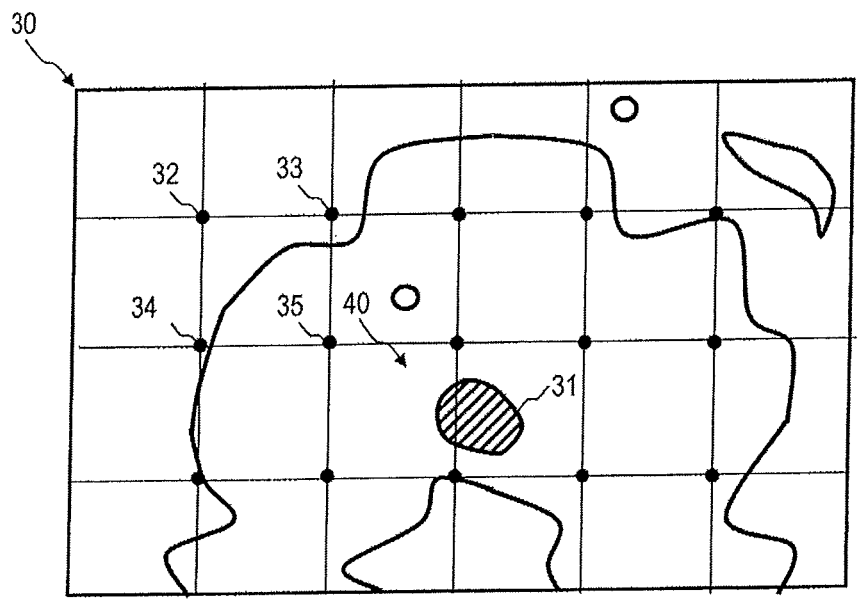
FIG. 2 shows the spatially resolved collection of Raman spectra of a sample according to an embodiment.

FIG. 2 schematically shows a tissue sample 30. The tissue sample is shown as a tissue section. However, the described techniques can also be used on tissue samples of other geometry, for example biopsy data obtained by punch biopsy. An aggressive tumor 31, which is shown only schematically, may be present. The tissue sample 30 may contain stroma of the tumor. In particular, it is not necessary for the described evaluation techniques to include tumor cells themselves in the tissue sample 30.

At a plurality of areas, which are shown as dots or filled circles, at least one Raman spectrum can be collected in each case. To improve the statistics, several Raman spectra can be acquired at each of the points. The signal acquisition and relative motion between a slide and optical components of the Raman spectroscopy system can be determined by the evaluation device 20 and controlled automatically. For example, Raman spectra can be detected at a plurality of separate small regions 32-35.

Although a regular arrangement of points is shown schematically in FIG. 2, at which the Raman spectra are collected, the detection can also take place on an irregular arrangement of points. Different patterns of points can be defined on which the Raman spectroscopy is performed. At least some of the items 32-35 may also be user definable. The evaluation device 20 may comprise a corresponding input interface with which a user-defined definition of those points is enabled, on each of which a Raman spectrum is to be collected.

The spatially resolved detection of the Raman spectra can occur at greater distances. According to embodiments, the spatially resolved collection of at least two Raman spectra may also occur on subcellular structures. At least two Raman spectra at different subcellular areas, such as cell nuclei and cytoplasm, can be acquired in one tissue sample, and passed to device 20 for evaluation.

The acquired Raman spectra can be evaluated in different ways. For example, for each of the Raman spectra, a statistical analysis, e.g. a principal component analysis or a hierarchical cluster analysis, may be applied. Accordingly, an assessment can be made as to whether a Raman spectrum or the majority of acquired Raman spectra are associated with an aggressive or a non-aggressive tumor. An assignment of individual Raman peaks or spectra patterns to biomarkers may or may not be performed.

The evaluation device 20 can be configured to determine from the entirety of the Raman spectrum whether an aggressive or non-aggressive tumor is present. A pattern or multiple patterns in the spectra obtained by statistical analysis, e.g. PCA or clustering techniques, may be used as a distinguishing criterion to distinguish aggressive and non-aggressive tumors. Such patterns may be defined by the location of multiple Raman peaks, their height, and/or the slope of the flanks. The evaluation device 20 can run a support vector machine to determine from the PCA results if an aggressive or non-aggressive tumor is present.

At least one and advantageously several of the evaluated Raman spectra are detected at a stroma 40 outside of the tumor 31.

Figure 3:
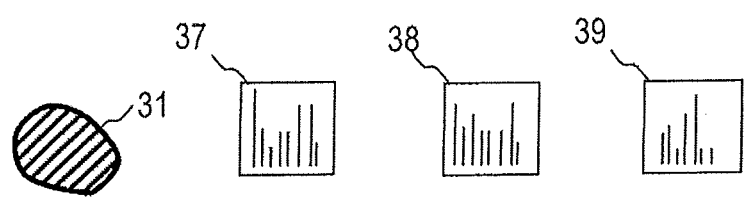
FIG. 3 shows the spatially resolved collection of Raman spectra of a sample according to an embodiment.

FIG. 3 shows by way of example the evaluation of Raman spectra 36-39 for the detection, and optionally, for the determination of the aggressiveness of tumors. The Raman spectra 36-39 can be detected at different positions. The location relative to the tumor 31 may also be unknown in advance. Dependent on the position, changes in the Raman spectra 36-39 are apparent; these changes indicate the presence of an aggressive or non-aggressive tumor.

Figure 4:
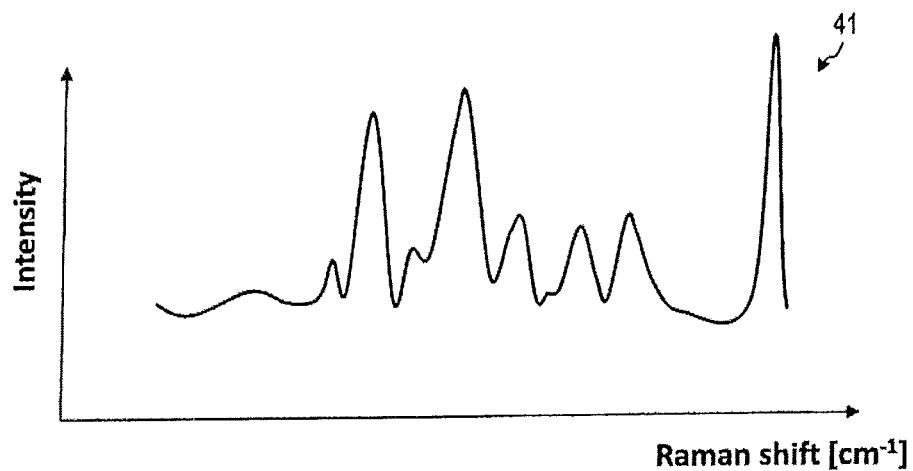
FIG. 4 shows an exemplary Raman spectrum, which is evaluated by a device according to an embodiment.

FIG. 4 shows an exemplary Raman spectrum 41, which was collected by device 1 from sample 9. For example, the device 1 may detect the Raman spectrum 40 at a point 33 of the tissue sample 30.

The evaluation device 20 can automatically detect a pattern of multiple Raman peaks characteristic of an aggressive tumor or non-aggressive tumor. The evaluation device 20 can be configured to analyze a characteristic wave number range or several characteristic wave number ranges in order to detect a pattern of Raman peaks characteristic of aggressive or non-aggressive tumors.

The evaluation device 20 can automatically recognize characteristic patterns of one or more Raman spectra. The wave numbers of Raman peaks positions, the peak height, the slope, the distances between the peaks, and/or combinations of peaks in one or more Raman spectra, can be detected to determine whether an aggressive or one non-aggressive tumor is present and/or to detect a tumor.

Based on the presence and, optionally, the intensity of the Raman signal at the Raman peaks characteristic for an aggressive tumor of the corresponding tissue or organ, it can be determined whether an aggressive tumor is present. Based on the intensity of the Raman signal at one or more of the Raman peaks, the evaluation device 20 can judge the tumor as to its to aggressiveness.

The Raman peaks shown schematically in FIG. 4 do not have to be individually recognized. In particular, the evaluation device 20 can subject the Raman spectrum in its entirety to a statistical analysis in order to detect whether the Raman spectrum is associated with an aggressive or a non-aggressive tumor. The analysis may include the application of a support vector machine.

It is also possible to record several Raman spectra on sample 9. A comparison of the different Raman spectra can be used to determine if an aggressive tumor is present and/or to assess the aggressiveness of the malignant tumor.

Figure 5:
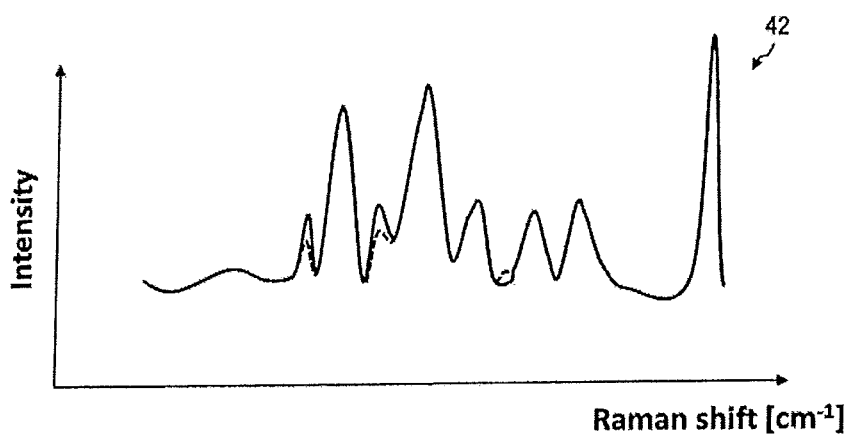
FIG. 5 shows another exemplary Raman spectrum, which is evaluated by a device according to an embodiment.

FIG. 5 shows, by way of example, another Raman spectrum 42, detected at a different position of the sample 9 than the Raman spectrum 41. The Raman spectrum 41 is also shown in FIG. 5 with broken lines for comparison.

For example, the further Raman spectrum 42 can be detected at a position 35, which is closer to the tumor than the position 33 where the Raman spectrum 41 was detected. Even if the location of the tumor or even if its presence is a priori not known, it can be determined by comparing the further Raman spectrum 42 at the position 35 and the Raman spectrum 41 at position 33, whether an aggressive tumor is present. It can also be determined in which direction the tumor is located relative to the positions 33, 35.

The intensity of the Raman signal and/or the spectral weight of the Raman peaks may be different in the Raman spectrum 42 from the intensity and/or the spectral weight in the Raman spectrum 41. For example, the intensity of the signal at one or more Raman peaks becomes greater as one approaches the position of the aggressive tumor, when the corresponding biomarker is more abundant in the immediate vicinity of the tumor than at more distant locations. The intensity of the signal at one or more other Raman peaks may diminish as one approaches the position of the aggressive tumor, if the corresponding biomarker is less present in the immediate vicinity of the tumor than at more distant locations.

The gradient of the Raman peaks does not have to be determined individually. In particular, the evaluator 20 may statistically analyze the Raman spectrum in its entirety to detect if the Raman spectrum is associated with an aggressive or a non-aggressive tumor. As will be described in more detail, for example, an assignment of Raman spectra to aggressive or non-aggressive tumors can be made automatically by the device based on the result of a statistical analysis without advance knowledge of the individual Raman peaks. The statistical analysis may include a support vector machine.

Figure 6:
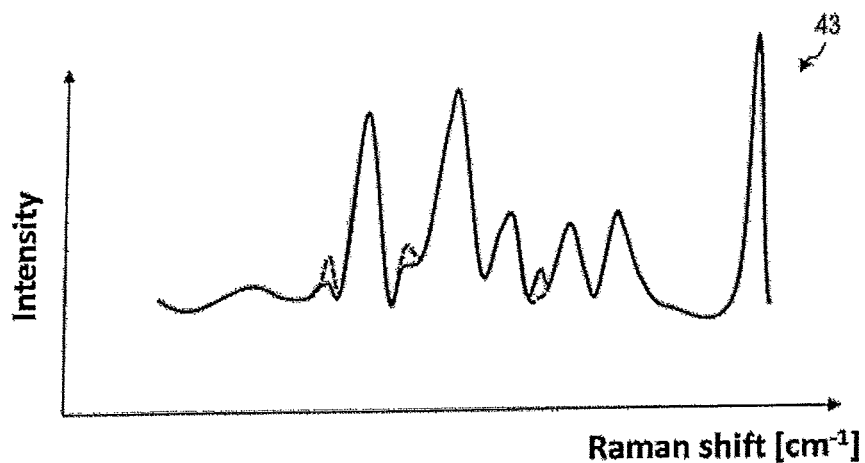
FIG. 6 shows another exemplary Raman spectrum, which is evaluated by a device according to an embodiment.

FIG. 6 shows, by way of example, another Raman spectrum 43, which is detected at another position of the sample 9 as the Raman spectrum 41. The Raman spectrum 41 is also shown with broken lines for comparison.

For example, the further Raman spectrum 43 can be detected at a position 32 which is farther from the tumor than the position 33 at which the Raman spectrum 41 was recorded. Although the location of the tumor or even its presence is not known a priori, it can be seen from a comparison of the Raman spectrum 43 at position 32 and the Raman spectrum 41 at the Position 33 determines whether a malignant tumor is present. It can also be determined in which direction the tumor is located relative to the positions 33, 35.

The intensity of the Raman signal and/or the spectral weight of the Raman peaks may be different in the Raman spectrum 43 from the intensity and/or the spectral weight in the Raman spectrum 41. For example, the intensity of the signal at one or more Raman peaks may decrease as it moves away from the position of the aggressive tumor if the corresponding biomarker is more abundant in the immediate vicinity of the tumor than at the more remote positions. The intensity of the signal at one or more other Raman peaks may increase as one moves away from the position of the aggressive tumor, if the corresponding biomarker is less strong in the immediate vicinity of the tumor than in more remote positions.

The gradient of the Raman peaks does not have to be determined individually. In particular, the evaluator 20 may statistically analyze the Raman spectrum in its entirety to detect if the Raman spectrum is associated with an aggressive or a non-aggressive tumor. As will be described in more detail, for example, assignment of Raman spectra to aggressive or non-aggressive tumors can be made automatically based on the result of a statistical analysis of the device, without the need to previously know the individual Raman peaks before the measurement.

The information content of several Raman spectra 41-43 can be combined to gain knowledge about the presence of a malignant tumor or its aggressiveness. The information of several Raman spectra 41-43 can each be further analyzed with a support vector machine to deduce a degree of aggressiveness or stages thereof.

In some embodiments, a local gradient of the intensity of the Raman signal may be determined at one or more of the Raman peaks characteristic of an aggressive tumor.

For this purpose, the gradient of the intensity or the spectral weight of the Raman peak in one, two or three dimensions can be determined mathematically for several points. In general, a determination of the gradient may be in N dimensions, where N may be equal to one or greater than one.

The gradient can also be based on the result of a further analysis of the Raman spectra. For example, by a statistical evaluation, each Raman spectrum can be assigned to a point in an N-dimensional data space, where N may be N>>1, for example N>100. The N-dimensional data space may be the data space spanned by the main components in a principal component analysis. From reference spectra it is possible to determine in which areas of the N-dimensional data space Raman spectra are arranged cluster-like for aggressive tumors and in which other areas of the N-dimensional data space Raman spectra for non-aggressive tumors are arranged cluster-like.

The location-dependent change of Raman spectra may include that, dependent on the location, further Raman peaks can emerge, indicating the presence of further biomolecules depending on the distance to the tumor and indicating the aggressiveness or non-aggressiveness of the tumor. Also, Raman peaks can vanish in a location-dependent manner (i.e., along a vector leading to or from a tumor), which can also be used to deduce the aggressiveness or non-aggressiveness of the tumor. The location-dependent variation of Raman spectra may involve shifting the point that can shift the corresponding Raman spectrum into an N-dimensional data space, where N>>1, for example N>100. The N-dimensional data space may be the data space spanned by the principal components in a principal component analysis.

To see if a Raman spectrum is indicating an aggressive or non-aggressive tumor, the evaluation device 20 may thus be arranged to perform a principal component analysis, cluster analysis, or other statistical analysis of at least one Raman spectrum. The evaluation device 20 may be configured to perform a support vector machine. The evaluation device 20 can be configured by the statistical analysis to quantitatively detect whether the Raman spectrum belongs to a cluster or region of the data space spanned by principal component analysis associated with the Raman spectra of aggressive tumors. The evaluation device 20 can be configured to detect quantitatively by the statistical analysis, whether the Raman spectrum belongs to a cluster or area of the data space spanned in the principal component analysis, which are assigned to the Raman spectra of non-aggressive tumors.

Figure 7:
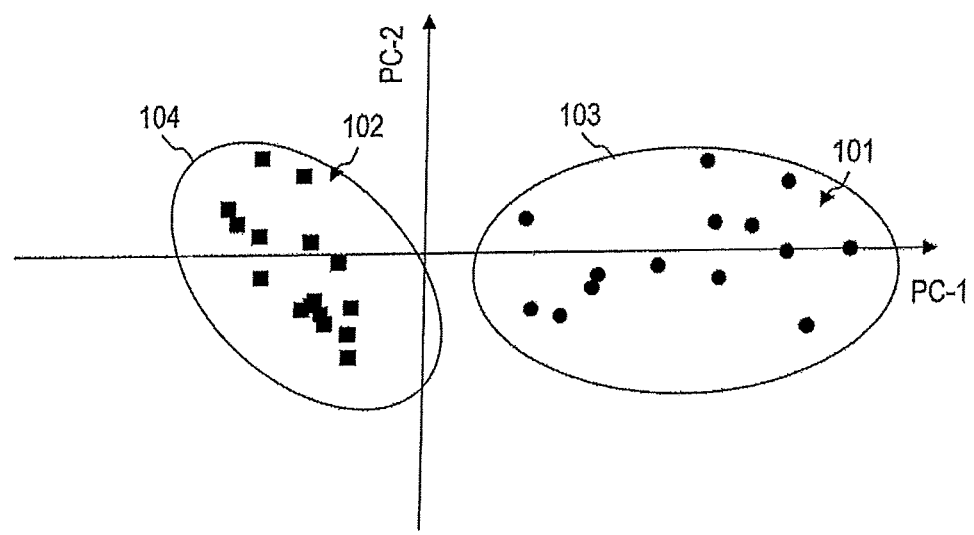
FIG. 7 illustrates a processing of captured Raman spectra by a device according to an embodiment.

FIG. 7 shows the results of a principal component analysis for aggressive and non-aggressive tumors. For the main component analysis, the respective detected Raman spectra at a plurality N>>1, for example N>100, are evaluated by Raman wave numbers. The N-dimensional vector, which corresponds to the Raman intensities at the N Raman wave numbers, defines a point in an N-dimensional data space.

By means of the principal component analysis (PCA) a coordinate transformation in the N-dimensional data space is determined in such a way that the different clusters or groups of Raman spectra in the transformed coordinate system clearly differ along one or more of the coordinate axes. These coordinate axes define the main components. The first major component PC-1 typically defines the axis with the most significant differences between the different groups of Raman spectra.

FIG. 7 shows how the data points 101, which correspond to Raman spectra of aggressive tumors, separate from data points 102, which correspond to Raman spectra of non-aggressive tumors, along the major component axis PC-1.

This separation, which occurs in the principal component analysis, can be used to determine from a Raman spectrum of a sample or from several Raman spectra of the sample whether they are associated with an aggressive or non-aggressive tumor. For this purpose, each Raman spectrum can be scanned at each of the N Raman wave numbers and then projected into a plane or a space, which is spanned by the principal component axes of the lowest orders. For example, based on the PC-1 component, i.e. the first major component, which shows the most pronounced differences between the Raman spectra of aggressive and non-aggressive tumors, determines whether an aggressive or a non-aggressive tumor is present. Alternatively, or additionally, it can be determined on the basis of the second main component PC-2 or another lower main component whether an aggressive or a non-aggressive tumor is present.

The determination of whether a Raman spectrum is characteristic of an aggressive or a non-aggressive tumor does not have to be based on individual Raman peaks, but can be based on a plurality of Raman spectra of uniformly or unevenly distributed Raman intensities in a plurality of Raman wave numbers. Principal component analysis or other statistical methods such as hierarchical or non-hierarchical cluster analysis can thus be exploited such that the Raman spectrum as a whole displays characteristics that are indicative of an aggressive or non-aggressive tumor and therefore serve as a "photonic fingerprint".

Through statistical analysis, such as the principal component analysis, in combination with a support vector machine, later discussed in more detail, cluster analysis can determine whether the pattern contained in the Raman spectrum or Raman peaks is characteristic of an aggressive or non-aggressive tumor. Alternatively or additionally, it can be determined whether that pattern in the Raman spectrum or Raman peaks is characteristic of the presence of a tumor.

The pattern in a Raman spectrum can be defined by an or several characteristics which are selected from the group consisting of: the wave number defining Raman peaks, the peak heights, the slope of the peaks, the distances between the peaks and/or combinations of peaks in one or more Raman spectra.

To evaluate one or more recorded Raman spectra of a sample, it can in each case be determined, by performing a principal component analysis in an area 103, which is associated with aggressive tumors, or another area 104, which is assigned to non-aggressive tumors, whether these are arranged in the data space.

Figure 8:
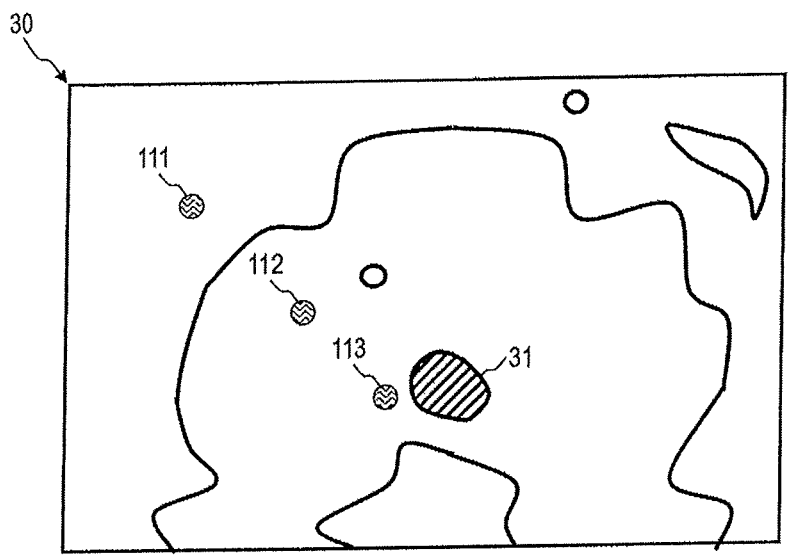
FIG. 8 illustrates a sample analyzed by a device according to an embodiment to illustrate the functioning of the device.

FIG. 8 shows a sample 30 with a tumor 31. In several regions 111, 112, 113, one or more Raman spectra are collected in each case for evaluation of the sample 30 by the device 1. One, several or all of the regions 111, 112, 113 may also lie in the stroma outside the tumor.

Each of the detected Raman spectra can be subjected to a statistical analysis by the evaluation unit of the device 1. For example, the Raman spectra can be evaluated at a plurality N of Raman wave numbers. The vectors containing the N Raman intensities at the N Raman wave numbers, where N>>1, can be projected by coordinate transformation in the data space with principal component axes defined based on reference spectra of aggressive and non-aggressive prostate tumors, with the lowest principal component(s) showing the clearest distinction between aggressive and non-aggressive prostate tumors.

Figure 9:
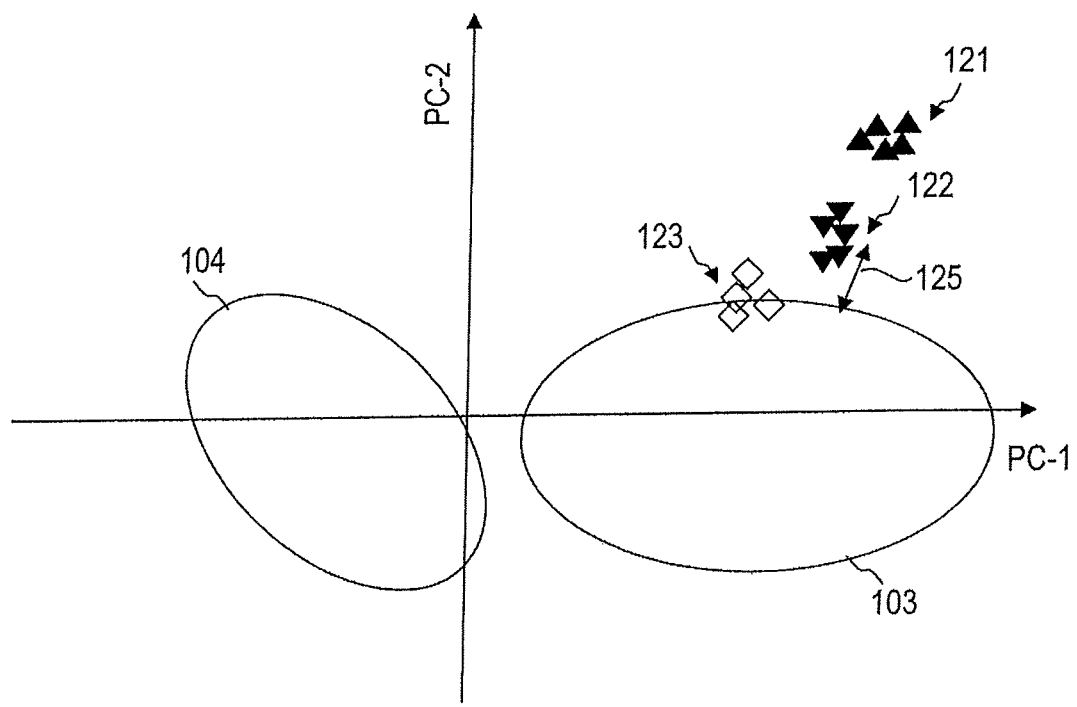
FIG. 9 illustrates a processing of captured Raman spectra by a device according to an embodiment.

FIG. 9 shows an example of the results of such an evaluation conducted by the device 1.

Data points 121 obtained in the data space of the principal component analysis for Raman spectra detected in a region 111 do not necessarily have to lie in or directly at one of the areas 103, 104 assigned to aggressive and non-aggressive prostate tumor tissue. Based on proximity to or an overlap with one of the areas 103, 104, however, an indication of the presence of an aggressive or non-aggressive prostate tumor can be obtained, even if the region 111 is located in the stroma.

Data points 122 obtained in the data space of the principal component analysis for Raman spectra detected in a region 112 do not necessarily have to lie in or directly at one of the areas 103, 104 assigned to aggressive and non-aggressive prostate tumor tissue. Based on proximity to or an overlap with one of the areas 103, 104, however, an indication of the presence of an aggressive or non-aggressive prostate tumor can be obtained, even if the region 112 is located in the stroma. Based on the fact that the data points 122 are at a distance 125 from the area 103 which is less than a distance of the data points 121 from the area 103, it can be concluded that the region 112 is closer to an aggressive prostate tumor than the region 111. This can be used for systematic determination of the location of the prostate tumor, even if the Raman spectra were not detected in a prostate tumor cell per se.

The distances between the data points 121, 122 and the area 103 can be determined by a wide variety of methods. For example, the focus of the data points 121 or 122 can be identified, and the distance thereof from the focus of the area 103 can then be determined. The focus of the data points 121 or 122 can be identified, and the distance thereof from the center or edge of the area 103 can then be determined. The distances of each of the data points 121 or 122 from the focus or edge of the area 103 can be determined, and the distances can then be averaged. Accordingly, distances from the area 104, which is assigned to non-aggressive prostate tumors, can also be determined. In this case, the distance from an edge of one of the areas 103, 104 is defined respectively as the minimum distance in the data space between the corresponding data point and all points in the data space lying at the edge of the corresponding areas 103, 104.

Data points 123 obtained in the data space of the principal component analysis for Raman spectra detected in a region 113 can lie in or directly at one of the areas 103, 104 assigned to aggressive and non-aggressive prostate tumor tissue. Based on the overlap, it can be determined that the region 113 is situated close to or overlapping an aggressive prostate tumor. Based on the fact that the data points 123 are at a distance from the area 103 which is less than a distance of the data points 121 from the area 103 and a distance 125 of the data points 122 from the area 103, it can be concluded that the region 113 is closer to an aggressive prostate tumor than the regions 111 and 112. This can be used for systematic determination of the location of the prostate tumor, even if the Raman spectra were not detected in a prostate tumor cell per se.

The principal component analysis can be combined with a support vector machine (SVM). For example, scanned and optionally already further processed intensities of the Raman spectrum may be further analyzed by means of a support vector machine to make an association of the Raman spectrum with aggressive and non-aggressive tumors possible.

Alternatively, or additionally to the principal component analysis, hierarchical or non-hierarchical cluster analyses can also be used respectively to determine whether a Raman spectrum as a whole shows greater similarity to the Raman spectra of reference samples containing aggressive tumors or the Raman spectra of reference samples not containing aggressive tumors.

In such cluster analyses, spectra can be grouped together or clustered based on a measure of similarity. Various measures of similarity can be used. For example, a cosine distance can be used to define a distance metric for Raman spectra.

In hierarchical cluster analyses, a tree of Raman spectra can be configured in which assessment of Raman spectra at the same or different nodes depends on the respective measure of similarity.

In hierarchical cluster analyses, after setting up a tree of Raman spectra, this tree can be divided into two or more subtrees. These subtrees can be assigned, for example, to aggressive tumors, non-aggressive tumors, or tumor-free tissue.

Setting up of the tree of reference spectra does not need to be carried out in every evaluation of detected Raman spectra. Rather, the corresponding tree of Raman spectra can be configured based on a plurality of reference spectra which were assigned to aggressive or non-aggressive tumors. In an evaluation of one or a plurality of Raman spectra detected in a sample, one can respectively determine in which subtree or which nodes the corresponding Raman spectra are to be classified based on the measure of distance. In this manner, the Raman spectrum detected for the sample can be assigned to an aggressive or non-aggressive tumor or a sample not containing a tumor.

Figure 10:
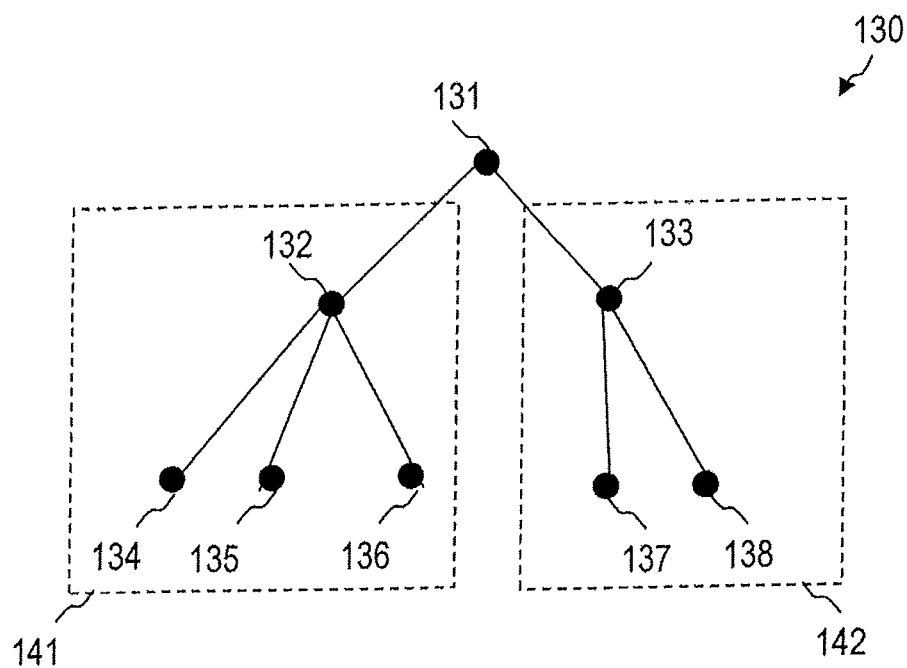
FIG. 10 illustrates a processing of captured Raman spectra by a device according to an embodiment.

FIG. 10 schematically illustrates the functioning of the evaluation unit of the device 1 in such a statistical evaluation, which comprises a cluster analysis.

By evaluation of a plurality of reference spectra, a tree 130 of Raman spectra is created either by the evaluation unit of the device 1 itself or also far from the device 1. The tree 130 contains a plurality of nodes 131-138. Raman spectra are assigned to the nodes 131-138 based on a measure of similarity, which for example can be based on a cosine distance.

The tree 130 can have a first subtree 141 assigned to aggressive tumors. The tree 130 can also have a second subtree 142 assigned to non-aggressive tumors.

In evaluation of a Raman spectrum or a plurality of Raman spectra detected in a sample 30, the evaluation unit 20 of the device 1 can calculate, based in each case on the distance measurement, to which of the leaf nodes 134-138 and/or inner nodes 132, 133 of the tree 130 the corresponding Raman spectrum is to be assigned. In this manner, Raman spectra can be assigned to aggressive or non-aggressive tumors even without prior knowledge of individually relevant wave numbers. At least one of the various leaf nodes 134-138 can, for example, be assigned to Raman spectra that were detected in the stroma outside an aggressive tumor. At least a further one of the various leaf nodes 134-138 can, for example, be assigned to Raman spectra detected in the stroma outside a non-aggressive tumor.

The techniques described with reference to FIGS. 7 to 10 can be used not only for samples that are tissue sections or punch biopsy specimens, but also for samples that are urine, sperm, lymphoid fluid, interstitial fluid or blood or are obtained therefrom.

Figure 11:
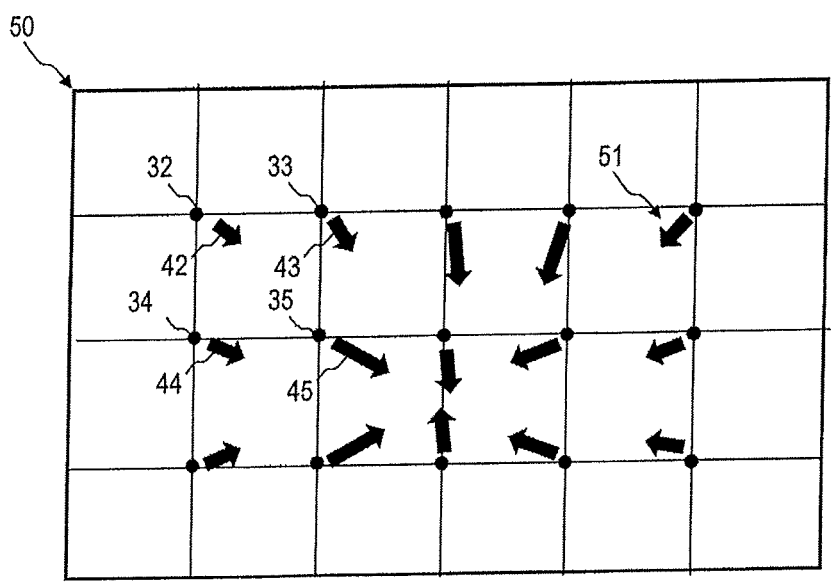
FIG. 11 illustrates a processing of captured Raman spectra by a device according to an embodiment.

FIG. 11 shows as an example the determination of a gradient field 50. For multiple sites in the tissue sample, the gradient field 50 indicates the strength, and optionally the direction of movement, of the intensity of a Raman peak 41-43 or a plurality of Raman peaks 41-43 characteristic of aggressive tumors. The plurality of gradients 51 can provide one piece of data in each case on the strength of the decrease or increase in the intensity of the Raman peaks, which is indicated in FIG. 11 by the length of the corresponding arrow. The plurality of gradients 51 can provide one piece of data in each case on the direction of the decrease or increase in the intensity of the Raman peaks, which is indicated in FIG. 11 by the direction of the corresponding arrow.

The gradients 42-45 shown as an example can be calculated from the intensity or the spectral weight of Raman peaks for biomarkers of the malignant tumor. As schematically shown in FIG. 11, the gradients provide information on the position of the tumor.

The gradients 51 need not be determined based on the intensities of the Raman peaks 41-43. For example, the gradients 51 can also be determined for the distance 125 shown by the data points in a statistical analysis of the areas 103, 104 in the data space to which aggressive or non-aggressive tumors are assigned.

Various techniques can be used to determine the intensity gradients or the spectral weight of Raman peaks in a spatially resolved manner. For example, for an area with coordinates (x,y), one can determine the gradient 51 according to $$\vec{g}(x, y) = \begin{pmatrix} [(|x + \Delta x, y) - |(x, y)]/\Delta x \\ [(|x, y + \Delta y) - |(x, y)]/\Delta y \end{pmatrix} \quad (1)$$

wherein data detection in two dimensions was taken as an example. In equation (1), g denotes the determined gradients. Here, I(x,y) denotes the intensity or the spectral weight of a Raman peak characteristic of an aggressive or non-aggressive tumor at coordinates (x,y). I(x+Δx, y) denotes the intensity or the spectral weight of the same Raman peak at coordinates (x+Δx, y).

I(x, y+Δy) denotes the intensity or the spectral weight of the same Raman peak at coordinates (x, y+Δy).

For the detection of Raman spectra on a regular, e.g. a rectangular grid, as shown by way of example in FIG. 2 by the reference number 30, the gradient can be determined as $$\vec{g}(x, y) = \begin{pmatrix} [(|x + a_x, y) - |(x - a_x, y)|/[2a_x] \\ [(|x, y + a_y) - |(x, y - a_y)|/[2a_y] \end{pmatrix} \quad (2)$$

where $a_x$ is the distance between adjacent data detection points along one coordinate axis and $a_y$ is the distance between adjacent data detection points along a further coordinate axis orthogonal thereto.

In a determination of the gradients based on the results of a statistical analysis, e.g. a principal component analysis, the corresponding equations (1) and (2) can also be used, wherein instead of I(x,y), the respective distance 125 of the Raman spectrum/spectra that were detected at the corresponding site can be used in the data space of the principal component analysis.

The position and also the aggressiveness of a malignant tumor can be determined even if no cancer cells are present in the sample 9 itself. For this purpose, the presence or optionally also the spatial change in Raman peaks, or the results of the statistical analysis of a plurality of Raman spectra as a function of the distance from the tumor, are used.

A support vector machine can be used to further process the gradient field to determine if an aggressive or non-aggressive tumor is present.

Figure 12:
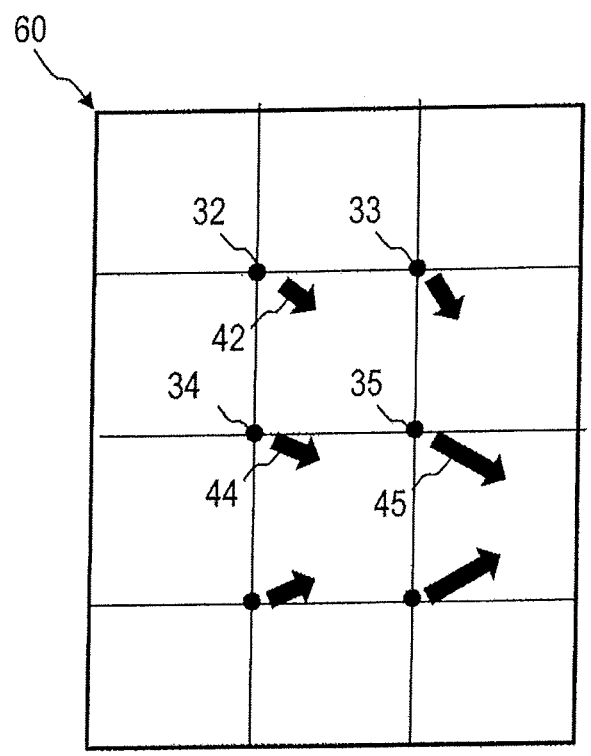
FIG. 12 illustrates a processing of captured Raman spectra by a device according to an embodiment.

FIG. 12 is a schematic diagram of a gradient field 60, which is automatically determined by the evaluation device 20 and which indicates the site-dependent change in intensity, the spectral weight of the Raman peaks 41-43, or the distances 125 from the area 103 that are characteristic of aggressive tumors. Even if the tumor is not contained in the sample, its location can be estimated based on the course of the local change in intensity or the spectral weight of the Raman peaks 41-43. Alternatively or additionally, the change in intensity or the spectral weight of the Raman peaks, which is determined from the sample, can be extrapolated so that the intensity or the spectral weight of the corresponding Raman peaks at a site of the tumor that is no longer contained in the sample can be estimated. This can be used for assessment of the tumor and/or stage determination.

Similar methods can also be used for the analysis of biopsy specimens, which for example are obtained by punch biopsy.

Figure 13:
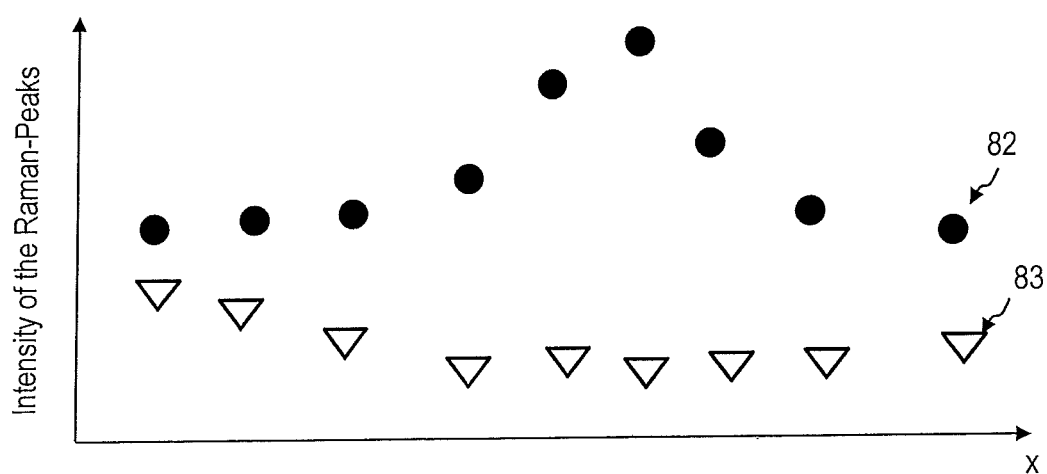
FIG. 13 illustrates a processing of captured Raman spectra by a device according to an embodiment.

FIG. 13 shows by way of example the intensity 82, 83 of a Raman peak, which is characteristic, for example, of an aggressive tumor, as a function of the location for a plurality of punch biopsies. The shown spatial variation of the intensity can be evaluated to determine in what quantity the corresponding biological marker, for example, on the tumor itself is present. The aggressiveness of the malignant tumor can be determined by calculation.

The electronic evaluation device can be configured to use the Raman spectrum it detects, for example using a characteristic pattern of the Raman spectrum at one or more wave numbers or wave number areas to determine the aggressiveness of the tumor.

Detection of the aggressiveness of the tumor does not have to be based on individual Raman peaks, but can also be carried out on the basis of a statistical analysis of one or more Raman spectra as a whole. A support vector machine can be used for evaluation. A priori knowledge of the assignment of Raman wave numbers and biomarkers is not required.

In this manner, one or more patterns defined by a Raman spectrum, such as position, height, slope, and a combination of multiple Raman peaks, are used to determine the presence and/or aggressiveness of a tumor. The pattern in a Raman spectrum can be defined by one or more characteristics selected from the group consisting of: the wave numbers where Raman peaks are located, the peak heights, the slope of the peaks, the distances between the peaks, and/or combinations of peaks in one or more Raman spectra.

Figure 14:
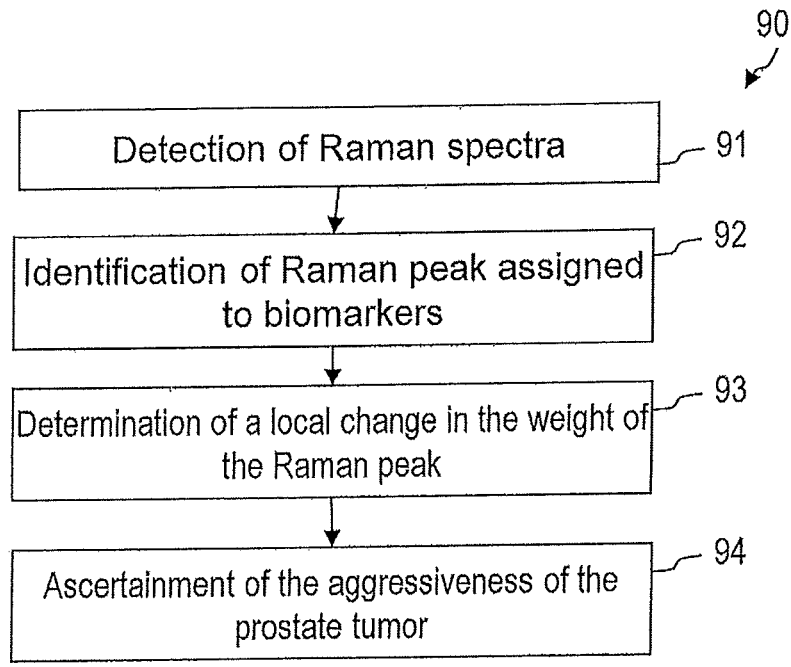
FIG. 14 is a flowchart of a method according to an embodiment.

FIG. 14 is a flow diagram of a method 90 according to an embodiment.

In step 91, at least one Raman spectrum of the sample 9 is detected. The light source 11 is controlled in such a way that an excitation beam 17 is produced. A plurality of Raman spectra can also be detected. For example, a plurality of Raman spectra can be detected at different sites in the same sample or in different samples in order to perform a grading or staging of a tumor. One or more of the Raman spectra can be detected in the stroma outside the tumor.

In step 92, the evaluation device 20 evaluates the detected Raman spectrum. The evaluation device 20 can identify at least one Raman peak or at least one pattern of Raman peaks characteristic of an aggressive tumor. At least one of the evaluated Raman spectra can be a Raman spectrum detected in the stroma outside the tumor.

In step 93, a spatial change in at least one Raman peak or at least one pattern of Raman peaks, which is characteristic of a biomarker indicative of prostate cancer can optionally be calculated.

In step 94, it is automatically determined whether a malignant tumor is present depending on the evaluation of the at least one Raman spectrum. The aggressiveness and/or stage of the tumor can be automatically determined.

Figure 15:
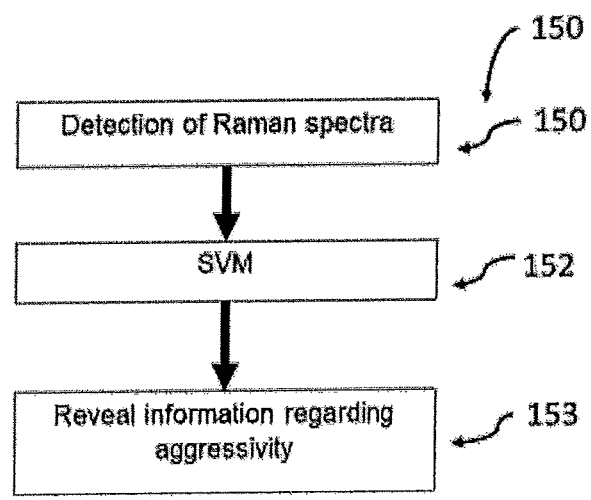
FIG. 15 is a flowchart of a method according to an embodiment.

FIG. 15 is a flow diagram of a method 150 according to an embodiment.

At step 151, at least one Raman spectrum of the sample 9 is detected. The light source 11 is controlled so that an excitation beam 17 is generated. It is also possible to record several Raman spectra. For example, several Raman spectra are recorded at different positions of the same sample or on different samples to perform a grading or staging of a tumor. One or more of the Raman spectra can be detected on stroma outside the tumor.

At step 152, the evaluation device 20 evaluates the detected Raman spectrum. In this case, the evaluation device 20 can recognize at least one Raman peak or at least one pattern of Raman peaks that is characteristic of an aggressive tumor. At least one of the evaluated Raman spectra can consist of a Raman spectrum detected on stroma outside the tumor. For evaluation, a support vector machine combined with a principal component analysis can be performed.

In step 153, depending on the evaluation of the at least one Raman spectrum, information is provided via an interface as to whether an aggressive tumor is present.

An aggressiveness and/or a stage of the tumor can be automatically determined and corresponding information may be obtained via the interface.

Figure 16:
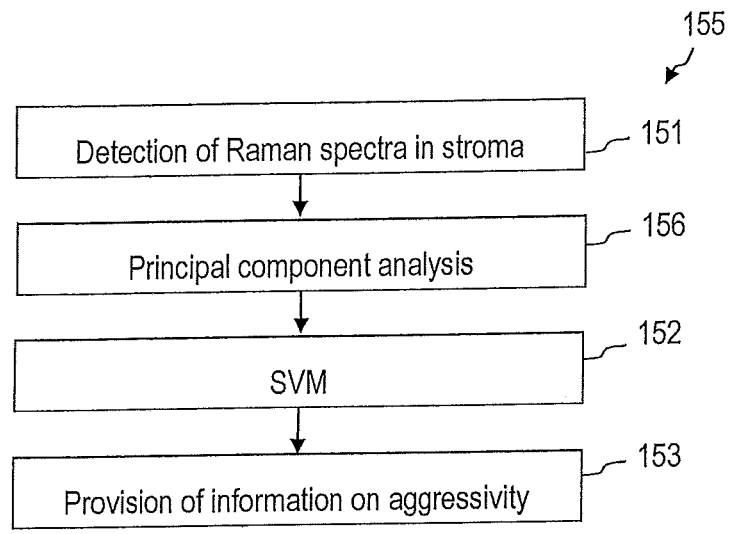
FIG. 16 is a flowchart of a method according to an embodiment.

FIG. 16 is a flow diagram of a method 155 according to an embodiment.

At step 151, at least one Raman spectrum of the sample 9 is detected. The light source 11 is controlled so that an excitation beam 17 is generated. It is also possible to record several Raman spectra. For example, multiple Raman spectra may be acquired at different positions of the same sample or on different samples to perform grading or staging of a tumor. One or more of the Raman spectra can be detected on stroma outside the tumor.

At step 156, the evaluation device 20 performs a principal component analysis of one or more acquired Raman spectra. Hereby the recorded Raman spectrum can be sampled at $N \gg 1$ wave numbers to yield a vector for the readings.

At step 152, the evaluation device 20 may execute a support vector machine to generate at least one Raman peak or at least one pattern of Raman peaks that are characteristic of an aggressive tumor. At least one of the Raman spectra evaluated may be a Raman spectrum detected on stroma outside the tumor.

In step 153, depending on the evaluation of the at least one Raman spectrum, information is provided via an interface as to whether an aggressive tumor is present. An aggressiveness and/or a stage of the tumor can be automatically determined and corresponding information can be obtained via the interface.

With the devices and methods according to the embodiments, a variety of pathological conditions can be detected and quantitatively evaluated by Raman spectroscopy on the stroma of a pathologically altered tissue.

Figure 17:
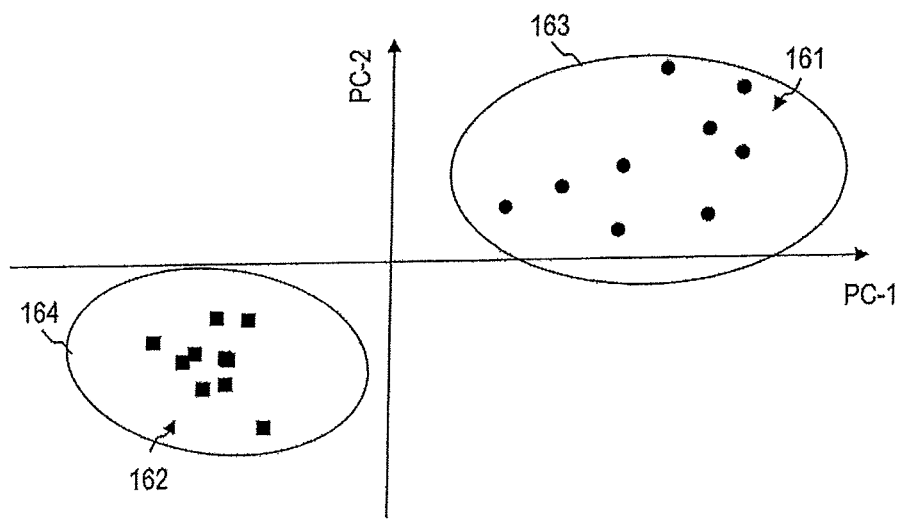
FIG. 17 illustrates the processing of captured Raman spectra by means of device according to an embodiment for the assessment of the aggressiveness or non-aggressiveness of a breast tumor.

FIG. 17 illustrates the processing of acquired Raman spectra by a device according to an embodiment for evaluating the aggressiveness or non-aggressiveness of a breast tumor. It is shown how the data points 161, which correspond to Raman spectra of aggressive breast tumors, are separated from data points 162, which correspond to the Raman spectra of non-aggressive breast tumors, along the main component axis PC-1.

By means of this separation, which occurs during the principal component analysis, it may be determined from a Raman spectrum of a sample or from several Raman spectra of the sample whether they are indicative of an aggressive or non-aggressive breast tumor. To this end, each Raman spectrum can be sampled at each of the N Raman wave numbers and then projected into the plane or space spanned by the major component axes of the lowest order. For example, based on the PC-1 component, i.e. the first main component, which shows the most pronounced differences between the Raman spectra of aggressive and non-aggressive breast tumors, determines whether an aggressive or a non-aggressive breast tumor is present. Alternatively, or additionally, the second major component PC-2 or other lower major component can be used to determine whether an aggressive or non-aggressive breast tumor is present. The principal component analysis can be combined with a support vector machine as described above.

The determination of whether the Raman spectrum is characteristic of an aggressive or non-aggressive breast tumor need not be based on individual Raman peaks, but can be performed on the basis of a plurality of the Raman spectra with evenly or unevenly distributed Raman intensities at a plurality of Raman wave numbers. With the principal component analysis, a support vector machine or other statistical methods such as hierarchical or non-hierarchical cluster analyzes, it can thus be deduced that the Raman spectrum as a whole has characteristics indicative of an aggressive or non-aggressive breast tumor and thus serve as a "photonic fingerprint".

The region 163 where data points corresponding to an aggressive breast tumor are located, and the region 164 where data points corresponding to non-aggressive breast tumors are located can be obtained by evaluating a plurality of Raman spectra detected at the stroma of breast tumors. In order to assess a breast tumor, Raman spectra acquired at the breast tumor stroma can be evaluated with a principal component analysis and optionally further processed, for example with a support vector machine, to determine if an aggressive or non-aggressive tumor is present. Similarly, a staging can be performed.

Figure 18:
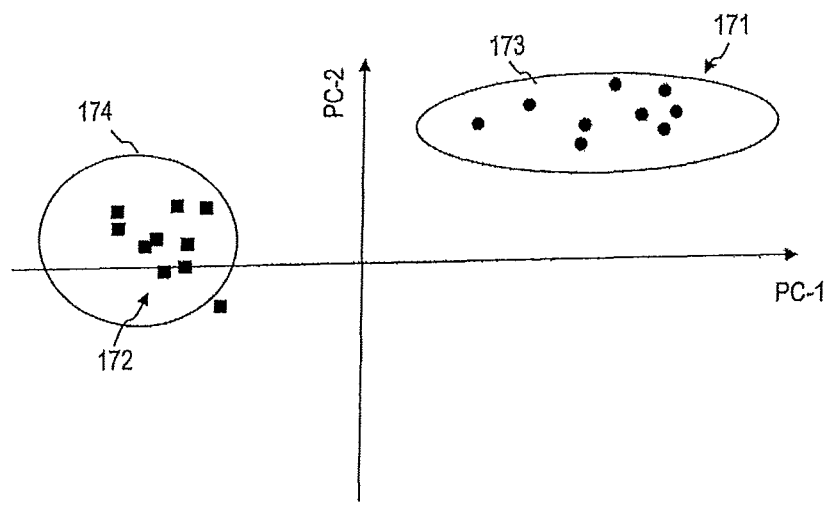
FIG. 18 illustrates a processing of captured Raman spectra by means of a device according to an embodiment for the assessment of the aggressiveness or non-aggressiveness of a pancreatic tumor.

FIG. 18 illustrates the processing of acquired Raman spectra by a device according to an embodiment for evaluating the aggressiveness or non-aggressiveness of a pancreatic tumor. It is shown how the data points 171, which correspond to the Raman spectra of aggressive pancreatic tumors, are separated from data points 172, which correspond to Raman spectra of non-aggressive pancreatic tumors, along the major component axis PC-1. The evaluation can be done using a support vector machine, as described above. The area 173 in which data points corresponding to an aggressive pancreatic tumor are arranged and the area 174 in which data points derived from a non-aggressive pancreatic tumor are arranged, can be compared by evaluating several Raman spectra recorded at the stroma of pancreatic tumors. To assess a pancreatic tumor, Raman spectra recorded at the stroma of the pancreatic tumor can be evaluated with a principal component analysis and optionally further processing, such as a support vector machine, to determine if an aggressive or non-aggressive tumor is present. Similarly, a staging can be performed.

Figure 19:
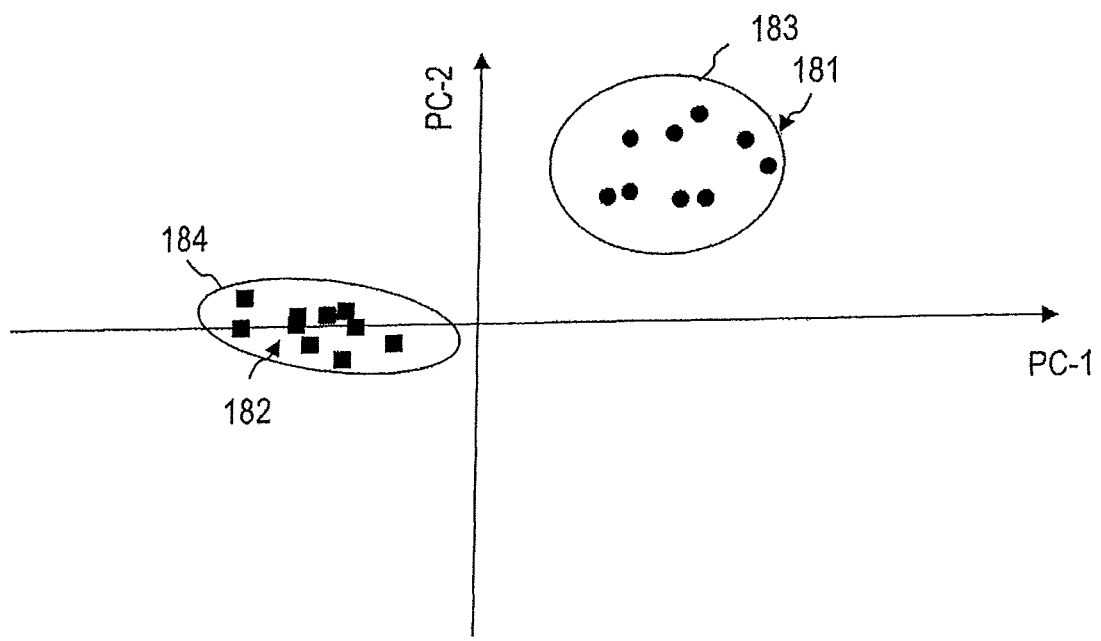
FIG. 19 illustrates the processing of captured Raman spectra by means of a device according to an embodiment to assess the aggressiveness or non-aggressiveness of a colon tumor.

FIG. 19 illustrates a processing of detected Raman spectra by a device according to an embodiment for evaluating the aggressiveness or non-aggressiveness of a colon tumor. FIG. 19 shows how the data points 181, which correspond to Raman spectra of aggressive colon tumors, are separated from data points 182, which correspond to Raman spectra of non-aggressive colon tumors, along the major component axis PC-1. The evaluation can be done using a support vector machine, as described above. The region 183, where data points corresponding to an aggressive colon tumor are located and the region 184 in which data points corresponding to a non-aggressive colon tumor are detected, can be obtained by evaluating a plurality of Raman spectra collected from colon tumors. To assess a colon tumor, Raman spectra acquired at the stroma of a colon tumor can be evaluated with a principal component analysis and optionally with further processing, such as a support vector machine, to determine if an aggressive or non-aggressive tumor is present. Similarly, a staging can be performed.

Figure 20:
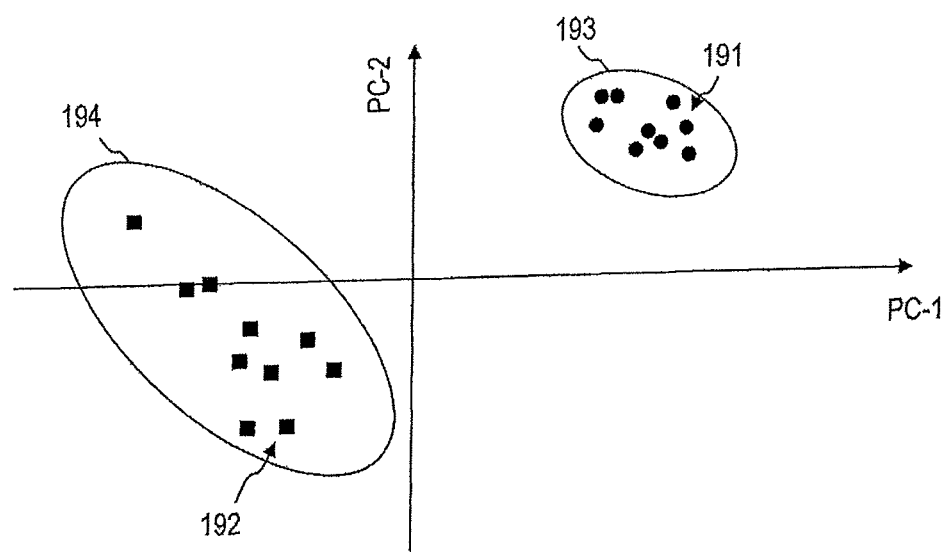
FIG. 20 illustrates a processing of captured Raman spectra by means of a device according to an embodiment to assess the aggressiveness or non-aggressiveness of a lung tumor.

FIG. 20 illustrates the processing of acquired Raman spectra by a device according to an embodiment to assess the aggressiveness or non-aggressiveness of a lung tumor. It is shown how the data points 191, which correspond to the Raman spectra of aggressive lung tumors, are separated from data points 192, which correspond to Raman spectra of non-aggressive lung tumors, along the major component axis PC-1. The evaluation can be carried out by means of a support vector machine, as described above. The area 193 in which data points corresponding to an aggressive lung tumor are arranged, and the region 194, where data points are arranged, which correspond to non-aggressive lung tumors, can be determined by evaluating several Raman spectra collected at the stroma of lung tumors. To assess a lung tumor, Raman spectra acquired at the stroma of the lung tumor can be analyzed with a principal component analysis and optionally by further processing, for example with a support vector machine, to evaluate whether an aggressive or non-aggressive tumor is present. Similarly, a staging can be performed.

Figure 21:
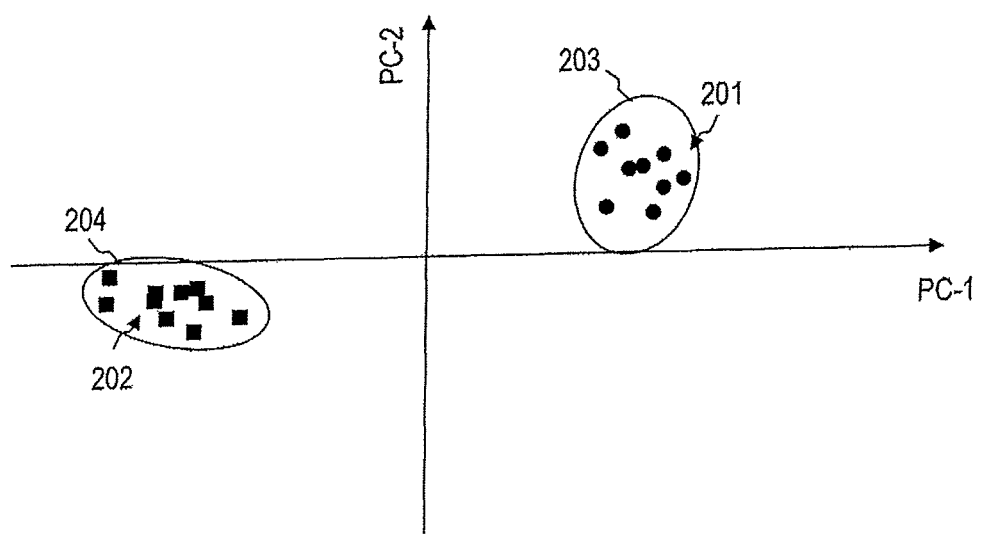
FIG. 21 illustrates the processing of captured Raman spectra by means of a device according to an embodiment for the assessment of the aggressiveness or non-aggressiveness of a thyroid tumor.

FIG. 21 illustrates a processing of detected Raman spectra by a device according to an embodiment to assess the aggressiveness or non-aggressiveness of a thyroid tumor. It is shown how the data points 201, which correspond to Raman spectra of aggressive thyroid tumors, are separated from data points 202, which correspond to Raman spectra of non-aggressive thyroid tumors, along the major component axis PC-1. The evaluation can be done by means of a support vector machine, as described above. The area 203 in which data points corresponding to an aggressive thyroid tumor are arranged, and the area 204 in which data points are arranged, which correspond to a non-aggressive thyroid tumor can be determined by evaluating several Raman spectra recorded at the stroma of a thyroid tumor. For evaluation of a thyroid tumor, Raman spectra acquired on the stroma of the thyroid tumor can be analyzed with a principal component analysis and optionally by further processing, for example a with a support vector machine, to determine if an aggressive or non-aggressive tumor is present. Similarly, a staging can be performed.

Figure 22:
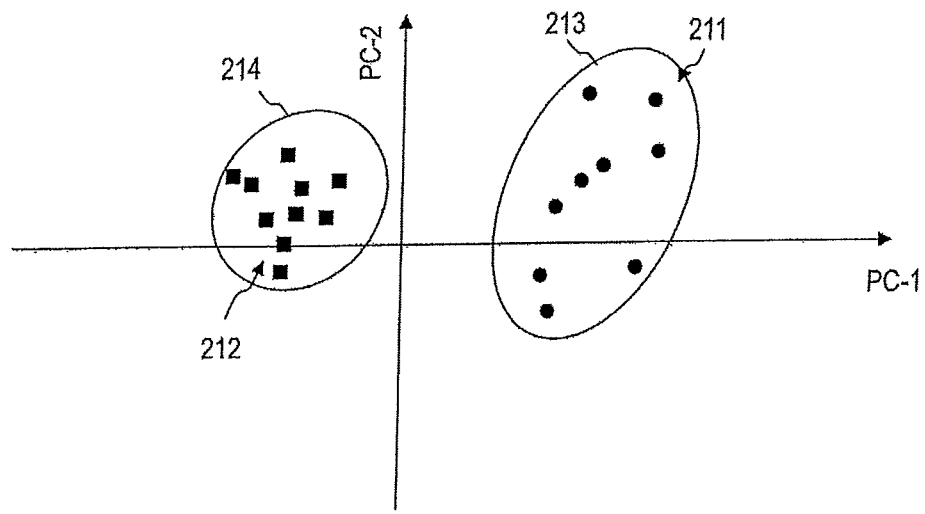
FIG. 22 illustrates the processing of captured Raman spectra by means of a device according to an embodiment to assess the aggressiveness or non-aggressiveness of a stomach tumor.

FIG. 22 illustrates a processing of acquired Raman spectra by a device according to an embodiment for evaluating the aggressiveness or non-aggressiveness of a stomach tumor. It is shown how the data points 211, which correspond to Raman spectra of aggressive stomach tumors, are separated from data points 212, which correspond to Raman spectra of non-aggressive stomach tumors, along the major component axis PC-1. The evaluation can be done using a support vector machine, as described above. The area 213, where data points are arranged, which correspond to an aggressive stomach tumor, and the area 214, where data points are arranged that correspond to a non-aggressive stomach tumor, can be determined by evaluating multiple detected Raman spectra at the stroma of a stomach tumor. For the assessment of a stomach tumor, Raman spectra detected on the stroma of a stomach tumor can be evaluated with a principal component analysis and optionally by further processing, for example, with a support vector machine, thus allowing the determination whether an aggressive or non-aggressive tumor is present. Similarly, a staging can be performed.

Figure 23:
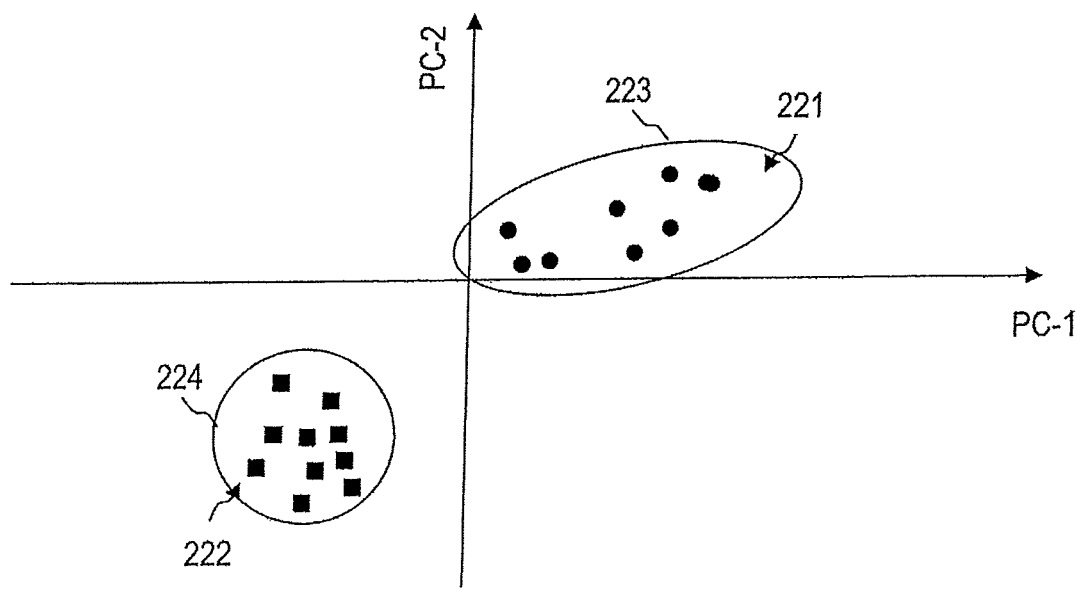
FIG. 23 illustrates a processing of captured Raman spectra by means of a device according to an embodiment for the assessment of the aggressiveness or non-aggression of an ovarian tumor.

FIG. 23 illustrates processing of acquired Raman spectra by a device according to an embodiment for evaluating the aggressiveness or non-aggressiveness of an ovarian tumor. It is shown how the data points 221, which correspond to Raman spectra of aggressive ovarian tumor, are separated from data points 222, which correspond to the Raman spectra of non-aggressive ovarian tumor, along the major component axis PC-1. The evaluation can be performed using a support vector machine, as described above. The region 223, where data points corresponding to aggressive ovarian tumors are located, and the region 224, where data points corresponding to non-aggressive ovarian tumors are located, can be obtained by evaluating a plurality of Raman spectra detected at the ovarian tumor stroma. To assess an ovarian tumor, Raman spectra acquired at the stroma of the ovarian tumor can be evaluated with a principal component analysis and optionally by further processing, such as a support vector machine, to determine if an aggressive or non-aggressive tumor is present. Similarly, a staging can be performed.

Figure 24:
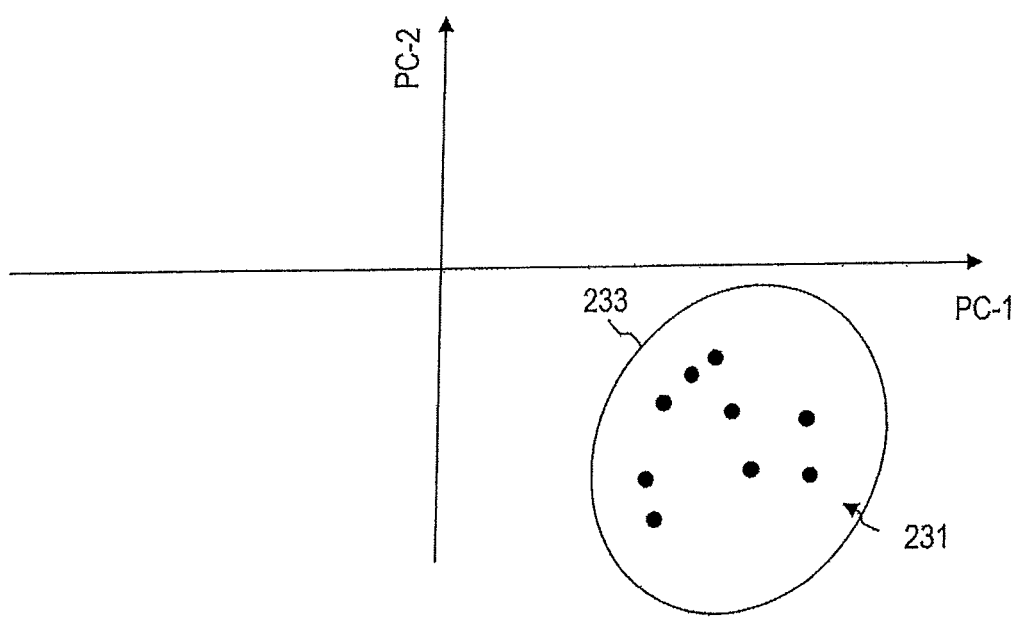
FIG. 24 illustrates the processing of captured Raman spectra by means of a device according to an embodiment for the detection of endometriosis.

FIG. 24 illustrates a processing of detected Raman spectra by a device according to an embodiment for the detection of endometriosis. It is shown how the data points 231, which correspond to Raman spectra of endometriosis patients, are arranged in a certain area 233 of the main component noise. The region 233 in which data points are arranged which correspond to the presence of endometriosis can be determined by evaluating a plurality of Raman spectra detected at the stroma.

To automatically differentiate between aggressive and non-aggressive tumor types, a data analysis with the help of a support vector machine with a linear kernel can be applied. This method searches for commonalities within individual groups from a training data set and creates a model. The algorithm also tries to find the largest distance between the groups. This model can then be used to assign unknown data sets to each group. Learning can be done automatically without a priori knowledge of the properties of the Raman spectra of aggressive and non-aggressive breast tumors, pancreatic tumors, colon tumors, lung tumors, thyroid tumors, stomach tumors and/or ovarian tumors. In the samples, the individual tissue types can be compared separately, i.e. tumor tissue of patients with aggressive tumor with patients with non-aggressive tumor and/or isolated stromal tissue of patients with aggressive tumor with non-aggressive tumor. For this purpose, data sets are compared, which include approximately the same number of measurements.

To estimate the quality of the model, a cross-validation can be performed for each data analysis. Two-thirds of the data set can be used here as a training data set. Then the remaining third is tested with the created model. The predicted group affiliations can then be compared to the actual group affiliations.

Accordingly, during training, statements about the reliability of the model to be applied can be made. For example, the overall hit rate, the sensitivity and/or the specificity of the model can be calculated.

Other configurations are possible. For example, supervised learning techniques may be used by which the evaluating device 20 automatically determines which patterns of Raman peaks are associated with aggressive or non-aggressive breast tumors, pancreatic tumors, colon tumors, lung tumors, thyroid tumors, stomach tumors, and/or ovarian tumors.

In devices and methods according to the described embodiments, the evaluation of Raman spectra may each comprise a comparison with Raman spectra in reference data associated with aggressive or non-aggressive tumors.

Alternatively or additionally, the reaction of tumor cells, stroma or other components of the sample may be detected on substances produced by a tumor. Accordingly, predictions on the presence of a tumor and/or a distinction of aggressive and non-aggressive tumors can be made.

While embodiments have been described in the context of specific tumors such as breast tumors, pancreatic tumors, colon tumors, lung tumors, thyroid tumors, stomach tumors and/or ovarian tumors, the devices and methods disclosed herein may also be used for the grading and staging of other tumors.

Devices and methods according to the embodiments can generally be used for the quantitative analysis of samples for identifying tumors without being limited to it. The devices and methods can be used in particular for the analysis of previously obtained samples, the production of the samples not being comprised by the analysis methods.

The invention claimed is:

1. A device for detecting or evaluating a pathological condition, comprising
 a Raman spectroscopy system;
 an electronic evaluation device which is configured to perform a detection or assessment of the pathological condition depending on an evaluation of at least one Raman spectrum detected in stroma; and
 at least one controllable motor operative to induce a relative movement between a stroma tissue sample and optical components of the Raman spectroscopy system in order to automatically capture the at least one Raman spectrum at a plurality of positions of the stroma tissue sample.

2. The device according to claim 1, wherein the electronic evaluation device is configured to perform the detection or assessment of a tumor depending on the evaluation of the at least one Raman spectrum detected in the stroma outside a tumor.

3. The device according to claim 2, wherein the electronic evaluation device is configured to retrieve reference data for detecting or evaluating the tumor depending on a tumor type of the tumor.

4. The device according to claim 2, wherein the tumor is selected from a group consisting of:
 a breast tumor,
 a pancreatic tumor,
 a colon tumor,
 a lung tumor,
 a thyroid tumor,
 a stomach tumor,
 an ovarian tumor.

5. The device according to claim 1, wherein the electronic evaluation device is configured to perform a grading of a tumor depending on the at least one Raman spectrum.

6. The device according to claim 1, wherein the electronic evaluation device is configured to determine, depending on the at least one Raman spectrum, whether a tumor is aggressive or non-aggressive.

7. The device according to claim 1, wherein the electronic evaluation device is configured to detect endometriosis via evaluation of the at least one Raman spectrum in the stroma of an endometrium.

8. The device according to claim 1, wherein the electronic evaluation device is configured to apply a support vector machine to data obtained from the at least one Raman spectrum.

9. The device according to claim 8, wherein the electronic evaluation device is configured to subject the at least one Raman spectrum to a principal component analysis and apply the support vector machine to identified major components.

10. The device according to claim 8, wherein the support vector machine has a linear kernel.

11. The device according to claim 1, comprising:
 a sample holder adapted to hold the tissue sample for Raman spectroscopy, wherein the device is configured to apply an excitation beam of the Raman spectroscopy system from a lower side of the sample holder to the tissue sample.

12. A method for detecting or evaluating a pathological condition, comprising
 detecting at least one Raman spectrum,
 evaluating the at least one Raman spectrum by an electronic computing device, wherein at least one Raman spectrum detected in stroma is evaluated by the electronic computing device for detection or assessment of the pathological condition; and
 inducing a relative movement between a stroma tissue sample and optical components of the Raman spectroscopy system in order to automatically capture the at least one Raman spectrum at a plurality of positions of the stroma tissue sample.

13. The method according to claim 12, wherein, depending on the evaluation of a Raman spectrum detected in the stroma outside a tumor, the detection or assessment of the tumor is performed.

14. The method according to claim 13, wherein the electronic evaluation device retrieves reference data, which are used for the detection or assessment of the tumor, depending on a tumor type.

15. The method according to claim 13, wherein the tumor is a breast tumor, a pancreatic tumor, a colon tumor, lung tumor, thyroid tumor, a stomach tumor, or an ovarian tumor.

16. The method according to claim 12, wherein the electronic computing device performs a grading of a tumor depending on the at least one Raman spectrum.

17. The method according to claim 12, wherein the electronic evaluation device determines, depending on the at least one Raman spectrum, whether a tumor is aggressive or non-aggressive.

18. The method according to claim 12, wherein the electronic evaluation device detects an endometriosis by evaluating the at least one Raman spectrum detected in the stroma of an endometrium.

19. The method according to claim 12, wherein the electronic evaluation device uses a support vector machine on data obtained from the at least one Raman spectrum.

20. The method according to claim 19, wherein the electronic evaluation device subjects the at least one Raman spectrum to a principal component analysis and applies the support vector machine to identified major components.

21. The method according to claim 19, wherein the support vector machine has a linear kernel.

22. The method according to claim 12, wherein an excitation beam of a Raman spectroscopy system is applied from a lower side of a sample holder to the stroma tissue sample.

* * * * *